United States Patent [19]

Harmening

[11] 4,112,070

[45] Sep. 5, 1978

[54] BLOOD PRESERVATION SYSTEM

[75] Inventor: Denise M. Harmening, Ellicott City, Md.

[73] Assignee: Research Corporation, New York, N.Y.

[21] Appl. No.: 804,603

[22] Filed: Jun. 8, 1977

[51] Int. Cl.$^2$ ............... A61K 35/14; A61K 35/18; C12B 3/00
[52] U.S. Cl. .................................. 424/101; 195/1.8
[58] Field of Search ..................... 195/1.8; 424/101

[56] References Cited

U.S. PATENT DOCUMENTS

| | | | |
|---|---|---|---|
| 2,833,691 | 5/1958 | Klaas et al. | 424/101 |
| 3,269,911 | 8/1966 | Gibbon et al. | 424/101 |
| 3,522,346 | 7/1970 | Chang et al. | 424/101 |

*Primary Examiner*—Sam Rosen
*Attorney, Agent, or Firm*—Haight & Huard

[57] ABSTRACT

The useful shelf life of living erythrocytes suitable for transfusion is extended by maintaining adequate ATP and 2,3-DPG levels using an insoluble polymer material as a source of inorganic phosphate ions during the storage period.

24 Claims, No Drawings

BLOOD PRESERVATION SYSTEM

BACKGROUND OF THE INVENTION

This invention relates to an improved erythrocyte preservation method and composition. More particularly, this invention relates to such improvements in the storage of whole blood and of packed blood cells suitable for transfusion.

The biochemical processes that occur during blood preservation all contribute to the diminished post transfusion erythrocyte survival ability statistically correlated with the duration of storage time. Maintenance of in vivo survival ability of red cells is closely correlated to glucose metabolism and specifically associated with the maintenance of higher levels of cellular ATP (Adenosine Tri Phosphate). It has been postulated that ATP levels preserve membrane integrity by maintaining proper ionic transport gradients across the red cell membrane, adequate lipid turnover rate, hemoglobin in a functional state and normal equilibrium of oxidized and reduced glutathione, along with synthesis of adequate amount of $NAD^+$ and $NADP^+$. (Nicotinamide Adenine Dinucleotide and its Phosphate.)

Several studies are under way incorporating various chemical additives along with CPD (citrate-phosphate-dextrose) anticoagulant to stimulate glycolysis, yielding a net increase in ATP levels. One of these chemical additives currently being studied is adenine. The incorporation of adenine along with CPD anticoagulant into stored blood appears to increase ADP (Adenosine Di-Phosphate) levels, thereby driving the glycolysis equilibrium towards the synthesis of ATP. However, adenine has an adverse effect on the maintenance of the levels of another important organic phosphate, namely 2,3DPG ( 2,3 diphosphoglycerate). Recent concern over the levels of ATP and 2,3DPG has become a controversial subject. Because the main objective of transfusing patients is to provide oxygen delivery to the tissues, the blood oxygen affinity, directly determined by 2,3DPG levels, may be of critical importance. Therefore, in providing patients with suitable blood for transfusion one must now evaluate red cell viability not only in terms of ATP levels but also 2,3DPG levels to insure a nearly normal oxygen affinity for adequate hemoglobin-oxygen transport function, the ultimate goal of red cell transfusion. The dependence of normal hemoglobin function on 2,3DPG levels in the red cell has been well documented. As a result, current research is also geared towards incorporation of chemicals into the CPD storage solution to increase 2,3DPG levels.

Some of these chemicals under current investigation include inosine, methylene blue, pyruvate, dihydroxyacetone and ascorbic acid, along with various combinations of these additives; see, for example, U.S. Pat. No. 3,795,581.

Various clinical observations during such conditions as congestive heart failure, right to left cardiac shunts and hypoxemia due to pulmonary disease support the assumption that hemoglobin oxygen affinity is an important factor in determining oxygen delivery in vivo. The transfused red cell, totally depleted of 2,3DPG, can regain half the normal level within about twenty-four hours but this reconditioning may not be rapid enough to be effective in a severely ill patient. Furthermore, it is not known whether the rate of resynthesis of 2,3DPG in the donor cells given to critically ill patients is comparable to that observed in normal recipients. There seems to be a direct correlation between the ability to compensate for low 2,3DPG levels (generally implying a strong hemoglobin-oxygen affinity) and the severity of the illness of the patient, as has been reported by Dennis, et al in Surgery 77 (6):741-747 (June, 1975).

Blood with nearly normal hemoglobin-oxygen affinity is thus preferable for use in massive transfusions, particularly in infants, older patients and patients with complicating cardiovascular and pulmonary disease.

The physiological effects of high oxygen-affinity 2,3DPG depleted red cells on the myocardial, cerebral, hepatic and renal functions have not yet been fully evaluated, but patients requiring massive transfusions seem to be most susceptible to the adverse effects due to very low levels of 2,3DPG; see Beutler, et al, Vox Sang. 20:403-13 (1970).

Although numerous investigations indicate that red cell levels of ATP and 2,3DPG can be better maintained when the two chief preservative solutions ACD (acid citrate dextrose) and CPD (citrate-phosphate-dextrose) are supplemented with adenine, inosine or both during storage at 4° C, this must be approached with some caution. As has been reported by Bunn, et al in New England J. Med 282:1414-21 (1970), a patient receiving three or four units of thus-supplemented blood may develop hyperuremia, which would persist for approximately twenty-four hours. As reported by Valeri in J. Med. (Basel) 5(5):278-291 (1974), a further cause for concern is the possible renal toxicity of 2,8-dioxyadenine, a metabolite of adenine. No matter which chemical is used with an ACD or CPD preservative solution, it appears that only a combination of various chemical additives will maintain 2,3DPG levels past the third week of storage. Such combinations of chemical additives present definite complications in terms of renal toxicity.

OBJECTS OF THE INVENTION

Accordingly, it is a general object of this invention to provide a blood preservation system substantially free of the above-indicated disadvantages of the current state of the art.

Another object of the present invention is to provide a blood preservation system which extends the shelf life of stored blood while simultaneously maintaining satisfactorily high levels of both ATP and 2,3DPG in the stored blood.

A further object of the present invention is a blood preservation system which promotes greater glucose utilization.

An additional object of the present invention is a blood preservation system which buffers the pH of stored blood to provide for more adequate erythrocyte enzyme activity.

Yet another object of the present invention is a blood preservation system in which shelf life extending additives can be easily removed prior to transfusion.

A still further object of the present invention is a blood preservation system which further reduces the risk of septecemia from transfusion.

Upon further study of the specification and appended claims, further objects and advantages of this invention will become apparent to those skilled in the art.

SUMMARY OF THE INVENTION

Briefly, the above and other objects, features and advantages of the present invention are attained in one aspect thereof by providing living erythrocytes stored in vitro with a water-insoluble polymer containing releaseable phosphate ions for supplying a physiologically acceptable, continuous source of metabolizable phosphate to said erythrocytes in an amount and at a rate sufficient to maintain both 2,3DPG and ATP levels suitable for transfusion. Preferably, the phosphate is released in an amount and at a rate sufficient to maintain said levels at least equal to those in the freshly drawn blood for at least 20 more, preferably at least 28, days of storage at 4° C. The phosphate source is separable by physical as opposed to chemical techniques, preferably by simple decantation or filtration.

DETAILED DISCUSSION

In accordance with the present invention, it has been found that insoluble polymeric material can be employed as a source of inorganic phosphate ions, particularly di-basic phosphate, in preservation of metabolizing erythrocytes. By providing means for sustained release of di-basic inorganic phosphate, 2,3DPG and ATP levels can be maintained at values sufficiently high for transfusion purposes for a period of time of at least twenty-eight days.

While not wishing to be bound by any theory of the invention, it is believed that both the dibasic phosphate ion source and the continual release thereof in a blood preservation system are essential to attain the objects of the present invention. For example, the use of inorganic phosphates alone without providing means for the systained, gradual release thereof does not achieve the desired results. Likewise, the use of phosphates other than a dibasic inorganic phosphate in a CPD blood storage system does not attain the desired results, as has been reported by Chanutin et al in Arch. Biochem. and Biophysics 121:96–102 (1967). Accordingly, the gradual supply of phosphate is believed to inter-react with hemoglobin and the byproducts of erythorocyte metabolism in a manner which extends the viability of the erythrocytes so as to increase the suitable storage period of erythrocyte solutions, e.g., whole blood, packed cells etc., for purposes of transfusion. While not wishing to be bound by any theory of the invention, it is believed that a continuous source of metabolizable phosphate promotes greater glucose utilization by producing an initial increase in pH; acts as a source of metabolizable phosphate to facilitate high levels of organic phosphate, both ATP and 2,3DPG; and acts as a buffer for the erythrocyte solution, maintaining a narrower pH range to insure adequate activity of erythrocyte enzymes. Inorganic phosphate alone will have a buffer effect but also often causes hemolysis. By using a resin system as a continuous source of metabolizable phosphate ions, additional chemical additives are not required and the physiologically acceptable resin particles can be physically separated by being filtered out at the time of transfusion. Furthermore, resin particles having a tendency to adsorb bacteria from solutions can be employed as the source of metabolizable phosphate, thereby minimizing the risk of septicemia acquired in the course of a transfusion.

It will be apparent to those skilled in the art to which the present invention pertains that a number of techniques can be employed to provide means for gradual release of metabolizable phosphate in accordance with present invention, e.g. microencapsulation, differentially degradable coatings, etc. However, presently preferred as a source of continually releasing metabolizable phosphate is a weakly basic anion exchange resin which has been equilibrated with the inorganic metabolizable phosphate ion. Preferred ion exchange resins have a macroreticular bead structure containing many large, discrete pores which facilitate maximum ion diffusion. Because the organic framework is insoluble in all common laboratory solvents and chemically inert, it is readily separated from blood prior to transfusion. Anion exchange resins, i.e., those possessing functional groups which can undergo reactions with anions in a surrounding solution, particularly weakly basic anion exchange resins, are preferred. For use in the blood preservation system of the present invention, such resins which have the additional properties of adsorbing acids from organic reaction mixtures, exchanging anions in a slightly acidic media, a high exchange capacity, low swelling properties and a tendency to adsorb bacteria from the surrounding solution are particularly advantageous. One such resin is commercially available under the trade name of Amberlite Ir-45 from Rohm and Haas Company, a weakly basic, polystyrene-polyamine type anion exchange resin having a styrenedivinylbenzene matrix. The hydroxyl ionic form can be replaced with a metabolizable phosphate ionic group by simple equilibration, with any desired concentration of metabolizable phosphate in solution, e.g. using 1M dibasic phosphate. The anion exchange resin may be used alone or in combination with other anion and/or cation exchange resins suitable for the intended purpose. As the particles can circulate freely in CPD blood storage bags and be filtered out at the time of transfusion, they are especially convenient for use in whole blood preservation.

With respect to the functionality of the ion exchange resin employed, polyamine functionality is preferred for the weakly basic anion exchange resins, the only presently known criteria being that the resin in its free base form must be suitable for the adsorption of acids from a weakly acidic organic mixture. The macroreticular structure is chemically stable and regenerable, and the functionality of polyamine anion exchange resins is suitable for exchanging hydroxyl for dibasic phosphate ions therein. A large number of such resins are commercially available, and include but are not limited to polystryrene-divinylbenzene polyamine functionalities such as Amberlite IRA-93, Stratabed 93, Amberlite IRA 94, Amberlite XE270, Amberlite XE299 and Amberlite IR 45. Phenolic polyamine weekly basic resins can be employed, e.g. Amberlite IRP-58, IRP-58m and the parent resin, Amberlite IR-4B. Likewise, acrylic ester anion exchange resins such as Amberlite XAD-7, XAD-8, XE236 and IRA-68 can be employed. Furthermore, the "condensate" type weakly basic anion exchange resins such as those sold under the trade names Amberlite IRA-47, IRA-47S and IRA-49 are also suitable, provided they meet the above criteria. While the insoluble bead form is preferred because of the ease of subsequent separation, suitable resins can be employed in the gel form if appropriate precautions are taken in separation from the whole blood prior to transfusion.

In order to provide a suitable, long-term source of divalent inorganic phosphate ions, the anion exchange resin is equilibrated with a solution of the desired phosphate ions using conventional techniques. The strength of the phosphate solution employed and the length of time required for equilibration will vary somewhat, as is known to those skilled in the art, depending on the particular physical and chemical properties of the specific anion exchange resin to be used. As previously indicated, the particular nature of the resin is not critical, so long as it meets the criteria of both acting ad a reservoir for dibasic phosphate ions and does not leave behind any physiologically unacceptable residues or byproducts. Any inert, physiologically compatable anion exchanger containing some form of a phosphorylated functional group will be suitable.

If desired, additional erythrocyte metabolism regulators can be employed in accordance with the present invention, either by adding them to the blood storage bag or other suitable container or by providing means for sustained release thereof, e.g. in a manner analogous to those techniques which can be used for sustained release of the divalent phosphate. Suitable such additives especially adapted for use in the CPD anticoagulant system include but are not limited to adenine, dihydroxyacetone and ascorbic acid, either individually or in combination with one or more of said additives, e.g. see U.S. Pat. No. 3,795,581 for details with respect to the use of dihydroxyacetone in blood preservation systems; Haematologia 9 (1-2) : 49–57 (1975) for the use of adenine; and the New England Journal of Medicine 291 (2) : 68–74 (July 11, 1974) for a summary of the current state of the art.

pH regulation plays a key role in not only liquid blood preservation systems but also all other types of blood preservation. Although alkaline liquid preservatives results in generally good 2, 3DPG maintenance, ATP levels rapidly decline under these conditions and therefore viability is poor. While acid liquid preservatives result in good ATP maintenance, 2,3DPG levels are rapidly depleted and therefore red cell function is poor. This need to regulate an adequate pH range for preserved red blood cells stems from the fact that pH can modify the rate at which the numerous array of enzymes associated with glucose metabolism function.

Three irreversible reactions are optimal sites for the control of the rate of the glycolytic pathway:

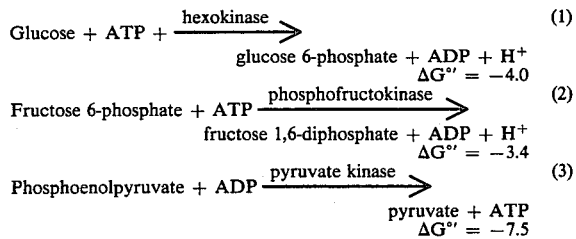

The rate of glycolysis is primarily controlled by the level of activity of phosphofructokinase. Achievement of an optimal pH to balance the activity of the glycolytic enzymes and the enzymes involved in the Rapport-Luebering Shunt, so that both systems are functioning, can be obtained using the resin blood preservation systems of the present invention.

Dibasic phosphate is preferred for charging the resin to provide two functions:

1. To serve as a buffer in the reaction

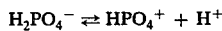

2. To serve as a source of inorganic phosphate ($P_i$) in the following ways:

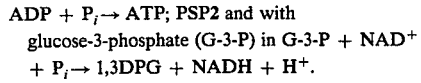

The dibasic phosphate can be used to achieve both of these functions; its K equilibrium is $6.2 \times 10^{-8}$, allowing the products and reactants to be in a ratio of about one at the approximate pH at which blood storage occurs.

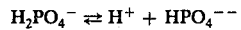

$$\frac{[H^+][HPO_4^=]}{[H_2PO_4^-]} = 6.2 \times 10^{-8}$$

$$\frac{[HPO_4^=]}{[H_2PO_4^-]} = \frac{6.2 \times 10^{-8}}{[H^+]}$$

The average optimal pH during the blood storage period is approximately 7.09, giving a hydrogen ion concentration of approximately $1 \times 10^{-7}$. Therefore, the ratio of $HPO_4^{--}$ to $H_2PO_4^-$ is approximately 0.62. Because the resin is releasing $HPO_4^{--}$ groups, the above reaction is driven to the left. This serves to utilize $H^+$ ions released during storage, thereby initially raising the pH and then maintaining it through a buffering effect. This allows maximum glucose utilization by increasing the enzyme activity of hexokinase (HK) and phosphofructokinase (PFK).

Furthermore, in an optimal pH range for blood storage, both phosphoglucokinase (PGK) and 2,3-diphosphoglyceromutase (2,3DPGM) activity can occur at the same time. The inorganic phosphate provided serves to shift the equilibrium of G-3-P→1,3DPG in the direction of 1,3DPG. Increases in 1,3DPG substrate serve to maintain adequate ATP levels as well as yield high 2,3-DPG concentrations. It is important that the concentration of 1,3DPG increases, as this is a controlling factor in the synthesis of 2,3DPG; the enzyme 2,3DPGM is not usually saturated with 1,3DPG. In contrast, the normal level of 3-phosphoglycerate (3-PG) in the red cell is nearly adequate to saturate the 2,3-DPG. Thus, the rate of synthesis of 2,3-DPG appears controlled not only by pH but also by the concentration of unbound 1,3DPG and 2,3DPG.

At present there is no in vitro measurement to predict satisfactorily the twenty-four hour post-transfusion survival value of a unit of preserved red cells, whether it be in terms of viability or functionality of the red blood cells. ATP concentrations serve as a convenient guide to evaluate the viability of preserved red blood cells, although adequate levels of ATP do not always correlate well with post-transfusion viability. An ATP level of 1.5 micromoles per gram of hemoglobin or higher is generally consistent with greater than seventy percent post-transfusion viability. Recently, the functionality of preserved red blood cells, in terms of adequate hemoglobin oxygen transport function, has been correlated with adequate levels of 2,3DPG. 2,3DPG depletion from stored blood serves as an explanation for the left shift of the oxygen dissociation curve observed in stored red blood cells. Although stored, 2,3DPG-depleted red blood cells may have a seriously impaired capacity to deliver oxygen to the tissues, the rate at which this storage defect is corrected is not known. Therefore, it is important to evaluate the function and viability of preserved red blood cells not only in terms of ATP levels (viability), but also 2,3DPG levels (function).

In the present invention, high levels of 2,3DPG as well as adequate levels of ATP are maintained throughout an entire twenty-eight day storage period without the incorporation of any metabolizable chemicals foreign to the CPD anticoagulant. The maintenance of both of these organic phosphates (ATP and 2,3DPG) for the entire storage period is not believed previously reported, although short term maintenance has been reported by Dawson et al in TRANSFUSION 16 (5) : 450–454 (Sept.-Oct. 1976) and in HAEMATOLOGIA 7 (3–4) : 295–300 (1973). While inorganic dibasic phosphate is presently preferred as a source of metabolizable phosphate in the present invention, it will be apparent that other phosphates, whether organic or inorganic, will likewise be suitable so long as they are gradually released and metabolizable, i.e. capable of being transported across the erythrocyte cell membrane and being taken up into ATP and/or 2,3DPG synthesis by various biochemical routes. Suitable such phosphates are well known to those skilled in the art and include but are not limited to inorganic dibasic phosphate, inorganic pyrophosphate, etc.

All the resin systems reported in the following Examples displayed a decrease in $HCO_3^-$ levels, $TCO_2$ (total carbon dioxide) and $PCO_2$ (partial pressure of carbon dioxide) levels. This is probably due to the resin exchanging the hydroxyl group for a bicarbonate ion, or direct binding of $CO_2$ to the resin. The chemical equilibrium reaction for bicarbonate with the enzyme carbonic anhydrase (c.a.) is:

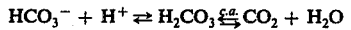
$$HCO_3^- + H^+ \rightleftarrows H_2CO_3 \overset{c.a.}{\rightleftarrows} CO_2 + H_2O$$

If $HCO_3^-$ is pulled off by the resin, this drives the reaction toward the formation of bicarbonate and hydrogen ions. This causes a decrease in the level of total and partial carbon dioxide pressures $TCO_2$ and $PCO_2$, as they are utilized to replenish the bicarbonate stores.

It will be apparent to those skilled in the art to which the invention pertains that the blood preservation system described herein can be employed by drawing fresh blood into a sterile container precharged with anticoagulant and a source of metabolizable phosphate as defined herein, e.g. when storing whole blood, or by adding the phosphate source to in vivo metabolizing erythrocytes, e.g. when storing packed cells.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLES

Amberlite IR-45 and IRC-50 were chose for experimental use as blood preservative mechanisms in this study. Three types of resin devices were utilized: IR-45 resin in varying amounts, IR-45 resin charged with dibasic phosphate and a monobed resin composed of a mixture of IR-45 and IRC-50 resins. Amberlite IR-45 resin, obtained from Rohm and Haas Co., is a weakly basic polystyrene-polyamine type anion exchange resin in the hydroxyl ionic form. This resin was placed in varying amounts into Fenwall 300ml transfer packs containing no anticoagulant.

Another type of resin exchange system was then devised utilizing the Amberlite IR-45 by charging this resin with 1M dibasic phosphate (anhydrous form) to remove the hydroxyl ionic group and replace it with a phosphate anion ($HPO_4^-$). The phosphate solution was run through a packed column of IR-45 resin particles until the pH of the original phosphate solution was reached in the supernatant collected from the resin column. Approximately 60% - 70% saturation of the resin particles was obtained. These charged resin particles were then placed into Fenwall 300ml transfer packs containing no anticoagulant.

A monobed resin exchange (mixture of two resins) was also devised utilizing IR-45 and IRC-50 resin particles. Amberlite IRC-50 is a synthetic cation exchange resin with carboxylic functionality in the hydrogen ionic form. This monobed resin system was then placed into Fenwall 300ml transfer bags containing no anticoagulant. A total of thirty 300ml capacity bags were prepared for use in this study. Five bags served as the controls and twenty-five bags served to house the resin devices. Each bag was cut at the bottom, the appropriate resin inserted, resealed and sterilized. The bags were coded 1 through 6 to designate the appropriate resin mechanism and lettered A through E to designate the various donors. The coding utilized was as follows:

Bags A1 through E1 — served as the controls, therefore contained no resin systems Bags A2 through E2 — contained 2.5gm of IR-45 resin Bags A3 through E3 — contained 5.0gm of IR-45 resin Bags A4 through E4 — contained 7.5gm of IR-45 resin Bags A5 through E5 — contained 4.0gm of phosphate charged IR-45 resin Bags A6 through E6 — contained 4.0gm of IR-45-TRC-50 monobed resin.

Controls involving the addition of phosphate alone without any resin system gave unsatisfactorily high hemolysis so that the blood was unsuitable for transfusion and accordingly were not included in the full study. Initial determinations were obtained on Day 1 and subsequent determinations weekly thereafter for up to 28 days. The results of each determination were statistically analyzed with the data tabulated in the Statistics Tables which follow the Results Tables. Each of the statistical determinations was calculated as to the significance of the effect of each mechanism alone in comparison with the control and the effect of storage time alone in comparison with the values on Day 1 as well as to the significance of the interaction between the various Mech and storage times. While several of the resin controls (Mech 2,3,4, & 6) show some improvement in one or more properties tested, only Mech 5 containing a source of metabolizable phosphate showed statistically significant improvement in all tested properties.

Five units of blood were collected into 450ml CPD bags and designated as donors A through E. The standards and methods published by the American Association of Blood Banks were adhered to for donor acceptance and processing, as well as for all other applicable aspects of the study. Each donor unit was then thoroughly mixed, weighed and divided into six equal amounts into the previously prepared and coded Fenwall 300ml transfer packs containing no anticoagulant on day zero.

The thirty bags were then stored at 4° C. and the temperature recorded each day. Aliquot samples were taken on days 1, 7, 14, 21 and 28. Control specimens were taken through the sample tubing and resealed each time. The rest of the specimens were taken off through the filter apparatus obtained from Plexitron RB 47 Surgical Blood Administration sets for separation of resin particles from the blood. A new filter for each donor was utilized on each day the sample specimens were taken off (days 1, 7, 14, 21 and 28). Each donor filter was rinsed with saline and dried with air between each mechanism. Agitation of the bags was performed via a side to side rotation before each sample was taken off.

Hemoglobin and hematocrit determinations were performed on the donors at the time of collection of the units into the 450ml CPD bags. Whole blood pH, $PCO_2$, $PO_2$, $TCO_2$ and $HCO_3^-$ were performed on the aliquot samples immediately after their removal. Whole blood dilutions of the aliquot samples for the ATP and 2,3DPG procedures were also performed immediately after removal and then stored at a temperature controlled $-70°$ C. for later determination. For plasma determinations of glucose, sodium and potassium, the aliquot specimens were then centrifuged, plasma removed and the plasma stored at $-70°$ C. for later batch determination.

Hematocrits were performed by the microhematocrit centrifuge. Hemoglobin determinations were performed by the standard cyanomethemoglobin procedure. Whole blood pH, $PCO_2$, $PO_2$, $TCO_2$, and $HCO_3^-$ were determined by the Corning 165 pH/Blood Gas Analyzer. Determinations were carried out by using the standards, procedures and controls set forth in the instruction manual provided by Corning. Plasma glucose determinations were performed on all specimens by batch testing by the Beckman Glucose Analyzer following the procedure recommended by the manufacturer. Extracellular sodium and potassium values were performed by batch testing and determined by the Beckman KLiNa Flame, again following the procedure outlined by the manufacture's manual. Analyses of concentrations of 2,3DPG and ATP were carried out by the principles of Lowry et al reported in J. Biol. Chem. 236: 2746 (1961) and I. Krimsky reported in Methods of Enzymatic Analysis, H. H. Bergmeyer (Ed.) p. 539 (1963) with the mechanized system described by Prins, et al in Biochem. Biophys. Acta 201 : 185 (1970) and the modified procedure of Dawson et al described in Report No. 995 of the U.S. Army Medical Research Laboratory, Fort Knox, Ky.

A two-way analysis of variance was performed for each chemical determination to examine:
1. The effect of the resin mechanisms;
2. The effect of storage time; and
3. The interaction between storage time and the resin devices.

Dunnett's Test utilizing one-tailed tests was used to compare each resin mechanism with the control; results are reported in the following Statistics Tables.

Table 1 lists the pH values, mean value, standard deviation and standard error for five donors stored over twenty-eight days in six different mechanisms. The results reveal that mechanisms of systems 2, 3, 4 and 5 all started at a higher pH than the control, while Mech 6 started at a lower pH. The data also seem to indicate that Mech 2 and 5 show a more gradual decline in pH as opposed to the control, while Mech 4 shows an increase and Mech 6 seems to follow the curve displayed by the control. There is a statistically significant difference among the effects of the mechanisms or systems; there is a significant difference due to the effect of time; and there is a significant difference due to the interaction between the different systems and time of storage. Dunnett's test revealed a significant difference between each mechanism as compared to the control (Mech 1). Mech 2, 3, 4 and 5 displayed a significant difference from the control in terms of an increase in pH, while Mech 6 showed a difference (not as great) from the control in terms of a decrease in pH.

Table 2 lists the plasma glucose concentrations, mean values, standard deviation and standard error for five donors stored over twenty-eight days in six different mechanisms. The concentrations are reported in milligrams per deciliter. The data reveal greater glucose utilization with Mech 2, 3, 4 and 5, with Mech 5 displaying the greatest glucose utilization, a measurement of glycolytic activity. Mech 6 follows the curve displayed by the control (Mech 1). There is a statistically significant difference among the effects of the mechanisms; there is a significant difference due to the effect of time; and there is a significant difference due to the interaction between the different systems and the time of storage. Dunnett's test revealed a significant difference between Mech 2, 3, 4 and 5 and the control (Mech 1), as the mechanisms displayed increased glucose utilization when compared with the control. There was no significant difference in terms of glucose utilization between Mech 6 and the control. Both Mech 6 and the control (Mech 1) showed slower glucose utilization, probably a sign of glycolytic impairment. The remaining resin systems, even without phosphate, showed some improvement in plasma glucose values.

Table 3 lists the 2,3DPG concentrations, mean values, standard deviation and standard error for five donors stored over twenty-eight days in six different mechanisms. The concentrations are reported in micromoles per gram of hemoglobin. The data reveal the maintenance of high values of 2,3DPG values for the entire twenty-eight day storage time with Mech 2, 3, 4 and 5, with Mech 5 displaying the highest maintained values. Mech 6 displayed a curve similar to the control (Mech 1). There is a statistically significant difference among the effects of the mechanisms; there is a significant difference due to the effect of time; and there is a significant difference due to the interaction between the different systems and the time of storage. Dunnett's test revealed a significant difference between Mech 2, 3, 4 and 5 and the control (Mech 1), as these Mech displayed higher maintained 2,3DPG values when compared to the control. There was no significant difference between Mech 6 and the control in terms of 2,3DPG concentrations. Both Mech 6 and the control displayed rapid depletion of 2,3DPG, reaching low levels by day fourteen.

Table 4 lists the ATP concentrations, mean values, standard deviation and standard error for five donors stored over twenty-eight days in six different mechanisms. The concentrations are reported in micromoles per gram of hemoglobin. The data display adequately maintained ATP levels for the entire twenty-eight day storage time with Mech 2, 3 and 5, with Mech 5 yielding the highest maintained values of the three Mech mentioned with a more gradual decline in ATP levels. Mech 4 yielded unacceptable ATP levels past day twenty-one, as 1.5 micromoles per gram of hemoglobin is the current minimally acceptable ATP level, which corresponds to seventy percent posttransfusion survival. Mech 6 displayed a curve similar to the control (Mech 1), and both the control and Mech 6 maintained high levels of ATP throughout the entire twenty-eight day storage period as compared to the other blood preservation systems. There is a statistically significant difference due to the effect of time; and there is a significant difference due to the interaction between the different systems and the time of storage. Dunnett's test revealed a significant difference between all the mechanisms and the control (Mech 1) in terms of a decrease in ATP levels; however, all the mechanisms except Mech 4 were above the acceptable ATP levels corresponding to seventy percent transfusion survival.

Table 5 lists the bicarbonate concentrations, mean values, standard deviation and standard error for five donors stored over twenty-eight days in six different mechanisms. The concentrations are reported in millimoles per liter. The data reveal that all of the mechanisms including the control displayed declines on bicarbonate concentrations as the blood was stored over the twenty-eight day storage period. There is a statistically significant difference among the effects of the mechanisms; there is a significant difference due to the effect of time; and there is a significant difference due to the interaction between the different systems and the time of storage. Dunnett's test revealed a significant difference between all the mechanisms and the control (Mech 1), in terms of a decrease in bicarbonate concentrations.

Table 6 lists the total carbon dioxide ($TCO_2$) concentrations, mean values, standard deviations and standard error for five donors stored over twenty-eight days in six different mechanisms. The concentrations are reported in millimoles per liter. The data reveal that all the mechanisms including the control displayed declines in $TCO_2$ concentrations as the blood was stored over the twenty-eight day storage period. There is a statistically significant difference among the effects of the mechanisms; there is a significant difference due to the effect of time; and there is a significant difference due to the interaction between the different systems and the time of storage. Dunnett's test revealed a significant difference between all the mechanisms and the control (Mech 1) in terms of a decrease in $TCO_2$ concentration.

Table 7 lists the plasma sodium concentrations, means values, standard deviations and standard error for five donors stored over twenty-eight days in six different mechanisms. The concentrations are reported in milliequivalents per liter. The data reveal that all the mechanisms including the control displayed declines, as well as fluctuations, in the sodium concentrations as the blood was stored over the twenty-eight day period. Mech 5 curve followed more closely than any other mechanism the curve displayed by the control. There is a statistically significant difference among the effects of the mechanisms; there is a significant difference due to the effect of time; and there is a significant difference due to the interaction between the different systems and the time of storage. Dunnett's test revealed a significant difference between all the mechanisms and the control (Mech 1) in terms of a decrease in plasma sodium concentrations. However, Mech 5 displayed the least amount of difference in comparison to the control.

Table 8 lists the plasma potassium concentrations, means values, standard deviations and standard error for five donors stored over twenty-eight days in six different mechanisms. The concentrations are reported in milliequivalents per liter. The data reveal that all the mechanisms including the control (Mech 1) display increases in plasma potassium concentrations. However, the control and Mech 6 display fluctuations while Mech 2, 3, 4 and 5 show increases and a consistant leveling off past day 7. There is no statistically significant difference among the effects of the mechanisms; there is a significant difference due to the effect of time; and there is a significant difference due to the interaction between the different systems and the time of storage. Dunnett's test revealed no significant difference between any of the mechanisms as compared to the control (Mech 1) in terms of increases and decreases in potassium levels. However, Mech 2 did show some decrease in potassium levels as compared to the control, while Mech 6 showed the highest increase in potassium levels, even though they were not statistically significant.

Table 9 lists the partial carbon dioxide ($PCO_2$) levels, mean values, standard deviations and standard error for five donors stored over twenty-eight days in six different mechanisms. The values are reported in millimeters of mercury. The data reveal that all the mechanisms except the control displayed decreases in the $PCO_2$ levels as the blood was stored for the twenty-eight day period. The control (Mech 1) displayed an increase in $PCO_2$ levels up to day fourteen, and then began to decline. There is a statistically significant difference among the effects of the mechanisms; there is a significant difference due to the effect of time; and there is a significant difference due to the interaction between the different systems and the time of storage. Dunnett's test revealed a significant difference between all the mechanisms and the control (Mech 1) in terms of a decrease in $PCO_2$ levels.

Table 10 lists the partial oxygen ($PO_2$) levels, mean values, standard deviations and standard error for five donors stored over twenty-eight days in six different mechanisms. The values are reported in millimeters of mercury. The data reveal that all the mechanisms including the control displayed fluctuations in the increases in $PO_2$ levels as the blood is stored throughout the twenty-eight day period. There is a statistically significant difference among the effects of the mechanisms and there is a significant difference due to the effect of time; but there is no significant difference due to the interaction between the different systems and the time of storage. Dunnett's test revealed a significant difference between Mech 4 and the control, while Mech 2, 3, 5 and 6 showed no significant difference when compared to the control.

RESULT TABLE I

| Determination: pH | | Donor and Mechanism Results, Mean, Standard Deviation, and Standard Error | | | | | | | | | |
|---|---|---|---|---|---|---|---|---|---|---|---|
| | | Time of storage | | | | | | | | | |
| Mech | Donor | Day 1 | | Day 7 | | Day 14 | | Day 21 | | Day 28 | |
| 1 | A | 7.066 | | 6.994 | | 6.876 | | 6.835 | | 6.707 | |
| | B | 7.075 | $x = 7.068$ | 6.948 | $x = 6.978$ | 6.844 | $x = 6.870$ | 6.759 | $x = 6.790$ | 6.766 | $x = 6.728$ |
| | C | 7.068 | $s = .02$ | 6.985 | $s = .03$ | 6.876 | $s = .02$ | 6.812 | $s = .04$ | 6.730 | $s = .02$ |
| | D | 7.098 | $s_E = .01$ | 7.010 | $s_E = .01$ | 6.903 | $s_E = .01$ | 6.797 | $s_E = .02$ | 6.720 | $s_E = .01$ |
| | E | 7.035 | | 6.951 | | 6.850 | | 6.747 | | 6.719 | |
| 2 | A | 7.158 | | 7.095 | | 7.111 | | 7.051 | | 6.957 | |
| | B | 7.114 | $x = 7.162$ | 7.060 | $x = 7.083$ | 7.079 | $x = 7.078$ | 7.070 | $x = 7.017$ | 7.041 | $x = 7.001$ |
| | C | 7.183 | $s = .03$ | 7.061 | $s = .03$ | 7.035 | $s = .03$ | 6.952 | $s = .05$ | 6.974 | $s = .05$ |
| | D | 7.197 | $s_E = .01$ | 7.121 | $s_E = .01$ | 7.076 | $s_E = .01$ | 6.982 | $s_E = .02$ | 6.967 | $s_E = .02$ |
| | E | 7.160 | | 7.076 | | 7.090 | | 7.028 | | 7.064 | |

RESULT TABLE I-continued

Determination: pH

Donor and Mechanism Results, Mean, Standard Deviation, and Standard Error — Time of storage

| Mech | Donor | Day 1 | | Day 7 | | Day 14 | | Day 21 | | Day 28 | |
|---|---|---|---|---|---|---|---|---|---|---|---|
| | A | 7.320 | | 7.209 | | 7.198 | | 7.182 | | 7.227 | |
| | B | 7.275 | $\bar{x}$ = 7.267 | 7.188 | $\bar{x}$ = 7.176 | 7.155 | $\bar{x}$ = 7.176 | 7.091 | $\bar{x}$ = 7.163 | 7.151 | $\bar{x}$ = 7.186 |
| 3 | C | 7.276 | s = .05 | 7.175 | s = .04 | 7.158 | s = .02 | 7.170 | s = .05 | 7.212 | s = .04 |
| | D | 7.272 | $s_E$= .02 | 7.197 | $s_E$= .02 | 7.204 | $s_E$= .01 | 7.141 | $s_E$= .02 | 7.135 | $s_E$= .02 |
| | E | 7.194 | | 7.109 | | 7.163 | | 7.232 | | 7.207 | |
| | A | 7.316 | | 7.149 | | 7.157 | | 7.209 | | 7.251 | |
| | B | 7.361 | $\bar{x}$ = 7.319 | 7.292 | $\bar{x}$ = 7.234 | 7.201 | $\bar{x}$ = 7.287 | 7.268 | $\bar{x}$ = 7.327 | 7.240 | $\bar{x}$ = 7.368 |
| 4 | C | 7.358 | s = .05 | 7.259 | s = .05 | 7.310 | s = 0.11 | 7.392 | s = .09 | 7.510 | s = 0.12 |
| | D | 7.328 | $s_E$= .02 | 7.220 | $s_E$= .02 | 7.373 | $s_E$= .05 | 7.335 | $s_E$= .04 | 7.370 | $s_E$= .06 |
| | E | 7.230 | | 7.250 | | 7.396 | | 7.429 | | 7.470 | |
| | A | 7.266 | | 7.172 | | 7.123 | | 7.070 | | 6.997 | |
| | B | 7.157 | $\bar{x}$ = 7.201 | 7.120 | $\bar{x}$ = 7.148 | 7.062 | $\bar{x}$ = 7.086 | 7.041 | $\bar{x}$ = 7.034 | 6.980 | $\bar{x}$ = 6.977 |
| 5 | C | 7.178 | s = .05 | 7.158 | s = .04 | 7.083 | s = .03 | 7.016 | s = .02 | 6.952 | s = .02 |
| | D | 7.231 | $s_E$= .02 | 7.187 | $s_E$= .02 | 7.102 | $s_E$= .01 | 7.029 | $s_E$= .01 | 6.964 | $s_E$= .01 |
| | E | 7.174 | | 7.104 | | 7.060 | | 7.014 | | 6.991 | |
| | A | 6.856 | | 6.842 | | 6.796 | | 6.672 | | 6.597 | |
| | B | 6.946 | $\bar{x}$ = 6.883 | 6.832 | $\bar{x}$ = 6.848 | 6.715 | $\bar{x}$ = 6.743 | 6.679 | $\bar{x}$ = 6.687 | 6.604 | $\bar{x}$ = 6.609 |
| 6 | C | 6.970 | s = .07 | 6.920 | s = .05 | 6.763 | s = .04 | 6.678 | s = .02 | 6.613 | s = .02 |
| | D | 6.857 | $s_E$= .03 | 6.866 | $s_E$= .02 | 6.755 | $s_E$= .02 | 6.712 | $s_E$= .01 | 6.646 | $s_E$= .01 |
| | E | 6.788 | | 6.780 | | 6.684 | | 6.693 | | 6.586 | |

RESULT TABLE 2

Determination: Glucose (mg/dl)

Donor and Mechanism Results, Mean, Standard Deviation, and Standard Error — Time of Storage

| Mech | Donor | Day 1 | | Day 7 | | Day 14 | | Day 21 | | Day 28 | |
|---|---|---|---|---|---|---|---|---|---|---|---|
| | A | 333 | | 322 | | 271 | | 236 | | 195 | |
| | B | 362 | $\bar{x}$ = 352 | 331 | $\bar{x}$ = 321 | 271 | $\bar{x}$ 226 =E268 | $\bar{x}$ = | 229 171 | x = | 186 |
| 1 | C | 354 | s = 12.0 | 325 | s = 7.30 | 278 | s = 8.82 | 248 | s = 15.8 | 207 | s = 15.8 |
| | D | 349 | $s_E$= 505.36 | 312 | $s_E$= 3.26 | 255 | $s_E$= 3.94 | 205 | $s_E$= 7.06 | 170 | $s_E$= 7.08 |
| | E | 362 | | 317 | | 263 | | 230 | | 185 | |
| | A | 343 | | 225 | | 224 | | 163 | | 131 | |
| | B | 346 | $\bar{x}$ = 343 | 217 | $\bar{x}$ = 228 | 222 | $\bar{x}$ = 229 | 142 | $\bar{x}$ = 159 | 100 | $\bar{x}$ = 121 |
| 2 | C | 248 | s = 5.77 | 219 | s = 10.9 | 254 | s = 14.5 | 180 | s = 15.6 | 151 | s = 20.2 |
| | D | 333 | $s_3$= 2.58 | 234 | $s_E$= 4.85 | 217 | $s_E$= 6.51 | 165 | $s_E$= 6.99 | 108 | $s_E$= 9.04 |
| | E | 343 | | 243 | | 227 | | 145 | | 116 | |
| | A | 348 | | 267 | | 172 | | 127 | | 500 | |
| | B | 344 | $\bar{x}$ = 335 | 262 | $\bar{x}$ = 262 | 217 | $\bar{x}$ = 201 | 128 | $\bar{x}$ = 143 | 81 | $\bar{x}$ = 83.4 |
| 3 | C | 349 | s = 20.4 | 273 | s = 13.9 | 224 | s = 22.3 | 200 | s = 31.9 | 119 | s = 25.5 |
| | D | 300 | $s_E$= 9.14 | 238 | $s_E$= 6.21 | 184 | $s_E$= 9.99 | 127 | $s_E$= 14.3 | 73 | $s_E$= 11.4 |
| | E | 336 | | 269 | | 210 | | 134 | | 94 | |
| | A | 351 | | 262 | | 186 | | 171 | | 78 | |
| | B | 363 | $\bar{x}$ = 349 | 253 | $\bar{x}$ = 257 | 177 | $\bar{x}$ = 182 | 104 | $\bar{x}$ = 127 | 59 | $\bar{x}$ = 76.8 |
| 4 | C | 345 | s = 14.0 | 266 | s = 9.04 | 203 | s = 13.1 | 134 | s = 27.0 | 106 | s = 19.2 |
| | D | 327 | $s_E$= 6.25 | 243 | $s_E$= 4.04 | 171 | $s_E$= 5.85 | 112 | $s_E$= 12.1 | 60 | $s_E$= 8.58 |
| | E | 358 | | 260 | | 173 | | 114 | | 81 | |
| | A | 315 | | 237 | | 160 | | 118 | | 69 | |
| | B | 335 | $\bar{x}$ = 308 | 240 | $\bar{x}$ = 236 | 171 | $\bar{x}$ = 170 | 103 | $\bar{x}$ = 110 | 51 | $\bar{x}$ = 64.4 |
| 5 | C | 309 | s = 19.4 | 249 | s = 13.0 | 198 | s = 17.9 | 125 | s = 12.2 | 105 | s = 24.7 |
| | D | 282 | $s_E$= 8.67 | 214 | $s_E$= 5.80 | 150 | $s_E$= 8.01 | 94 | $s_E$= 5.46 | 42 | $s_E$= 1.10 |
| | E | 301 | | 238 | | 170 | | 108 | | 55 | |
| | A | 362 | | 322 | | 256 | | 248 | | 222 | |
| | B | 340 | $\bar{x}$ = 344 | 333 | $\bar{x}$ = 320 | 291 | $\bar{x}$ = 270 | 263 | $\bar{x}$ = 246 | 208 | $\bar{x}$ = 214 |
| 6 | C | 344 | s = 10.6 | 320 | s = 8.96 | 274 | s = 15.4 | 271 | s = 21.7 | 228 | s = 10.7 |
| | D | 336 | $s_E$= 4.76 | 308 | $s_E$= 4.00 | 254 | $s_E$= 6.87 | 220 | $s_E$= 9.70 | 210 | $s_E$= 4.77 |
| | E | 337 | | 318 | | 276 | | 229 | | 202 | |

RESULT TABLE 3

Determination: 2,3 DPG (μM/gHb)

Donor and Mechanism Results, Mean, Standard Deviation, and Standard Error — Time of Storage

| Mech | Donor | Day 1 | | Day 7 | | Day 14 | | Day 21 | | Day 28 | |
|---|---|---|---|---|---|---|---|---|---|---|---|
| | A | 12.59 | | 9.26 | | 2.59 | | 0.74 | | 0.37 | |
| | B | 14.61 | $\bar{x}$ = 12.80 | 10.39 | $\bar{x}$ = 8.65 | 5.52 | $\bar{x}$ = 2.94 | 0.97 | $\bar{x}$ = 0.76 | 0.65 | $\bar{x}$ = 0.41 |
| 1 | C | 10.14 | s = 1.65 | 5.59 | s = 1.89 | 0.70 | s = 1.72 | 0.350 | s = 0.27 | 0.35 | s = 0.13 |
| | D | 13.29 | $s_E$= 0.74 | 9.79 | $s_E$= 0.84 | 3.15 | $s_E$= 0.77 | 0.70 | $s_E$= 0.12 | 0.35 | $s_E$= 0.06 |
| | E | 13.36 | | 8.22 | | 2.74 | | 1.03 | | 0.34 | |
| | A | 14.44 | | 10.37 | | 16.67 | | 18.52 | | 15.19 | |
| | B | 15.26 | $\bar{x}$ = 13.85 | 12.34 | $\bar{x}$ = 12.18 | 16.88 | $\bar{x}$ = 15.88 | 17.21 | $\bar{x}$ = 1617 | 15.26 | $\bar{x}$ = 13.72 |
| 2 | C | 12.59 | s = 1.09 | 12.24 | s = 1.09 | 14.69 | s = 0.97 | 12.59 | s = 2.21 | 10.14 | s = 2.32 |
| | D | 12.94 | $s_E$= 0.49 | 13.29 | $s_E$= 0.49 | 16.08 | $s_E$= 0.43 | 16.08 | $s_E$= 0.99 | 12.59 | $s_E$= 1.04 |
| | E | 14.04 | | 12.67 | | 15.07 | | 16.44 | | 15.41 | |
| | A | 8.15 | | 6.67 | | 16.30 | | 17.78 | | 13.33 | |
| | B | 15.58 | $\bar{x}$ = 13.43 | 12.01 | $\bar{x}$ = 11.44 | 16.56 | $\bar{x}$ = 16.36 | 17.21 | $\bar{x}$ = 17.34 | 14.94 | $\bar{x}$ = 13.71 |
| 3 | C | 13.29 | s = 3.16 | 11.89 | s = 2.77 | 15.73 | s = 0.52 | 16.78 | s = 0.44 | 12.94 | s = 0.78 |
| | D | 16.08 | $s_E$= 1.41 | 12.94 | $s_E$= 1.24 | 17.13 | $s_E$= 0.23 | 17.13 | $s_E$= 0.20 | 13.99 | $s_E$= 0.35 |
| | E | 14.04 | | 13.70 | | 16.10 | | 17.81 | | 13.36 | |
| | A | 7.41 | | 12.96 | | 19.63 | | 18.15 | | 13.33 | |
| | B | 13.64 | $\bar{x}$ = 12.75 | 12.66 | $\bar{x}$ = 12.48 | 15.58 | $\bar{x}$ = 15.86 | 15.91 | $\bar{x}$ = 15.84 | 12.66 | $\bar{x}$ = 12.98 |
| 4 | C | 12.94 | s = 3.16 | 11.54 | s = 0.75 | 13.64 | s = 2.26 | 14.69 | s = 1.37 | 11.89 | s = 0.78 |
| | D | 15.73 | $s_E$= 1.41 | 11.89 | $s_E$= 0.34 | 15.73 | $s_E$= 1.01 | 15.38 | $s_E$= 0.61 | 13.99 | $s_E$= 0.35 |

RESULT TABLE 3-continued

Determination: 2,3 DPG (μM/gHb)

Donor and Mechanism Results, Mean, Standard Deviation, and Standard Error

Time of Storage

| Mech | Donor | Day 1 | | | Day 7 | | | Day 14 | | | Day 21 | | | Day 28 | | |
|---|---|---|---|---|---|---|---|---|---|---|---|---|---|---|---|---|
| 5 | E | 14.04 | | | 13.36 | | | 14.73 | | | 15.07 | | | 13.01 | | |
|  | A | 11.11 | | | 14.07 | | | 16.30 | | | 17.41 | | | 14.07 | | |
|  | B | 12.67 | x = | 12.60 | 14.61 | x = | 13.23 | 17.53 | x = | 16.49 | 17.21 | x = | 16.72 | 17.21 | x = | 15.42 |
|  | C | 11.89 | s = | 1.22 | 11.54 | s = | 1.18 | 15.38 | s = | 0.85 | 16.08 | s = | 0.75 | 13.29 | s = | 1.66 |
|  | D | 14.34 | $s_E=$ | 0.54 | 12.94 | $s_E=$ | 0.53 | 17.13 | $s_E=$ | 0.38 | 17.13 | $s_E=$ | 0.33 | 16.08 | $s_E=$ | 0.74 |
|  | E | 13.01 | | | 13.01 | | | 16.10 | | | 15.75 | | | 16.44 | | |
| 6 | A | 11.85 | | | 4.44 | | | 4.07 | | | 3.33 | | | 2.96 | | |
|  | B | 14.61 | x = | 12.93 | 6.49 | x = | 4.69 | 1.95 | x = | 2.18 | 2.27 | x = | 2.29 | 2.29 | x = | 3.05 |
|  | C | 10.49 | s = | 1.81 | 3.85 | s = | 1.04 | 1.05 | s = | 1.13 | 1.40 | s = | 1.06 | 1.75 | s = | 0.96 |
|  | D | 14.69 | $s_E=$ | 0.81 | 4.55 | $s_E=$ | 0.47 | 2.10 | $s_E=$ | 0.51 | 3.85 | $s_E=$ | 0.47 | 3.15 | $s_E=$ | 0.43 |
|  | E | 13.01 | | | 4.11 | | | 1.71 | | | 3.77 | | | 4.45 | | |

RESULT TABLE 4

Determination: ATP (μM/gHb)

Donor and Mechanism Results, Mean, Standard Deviation, and Standard Error

Time of Storage

| Mech | Donor | Day 1 | | | Day 7 | | | Day 14 | | | Day 21 | | | Day 28 | | |
|---|---|---|---|---|---|---|---|---|---|---|---|---|---|---|---|---|
| 1 | A | 4.59 | | | 4.89 | | | 4.15 | | | 4.52 | | | 3.78 | | |
|  | B | 5.95 | x = | 5.20 | 5.52 | x = | 5.36 | 5.97 | x = | 5.27 | 5.26 | x = | 5.05 | 5.26 | x = | 4.71 |
|  | C | 4.69 | s = | 0.56 | 5.10 | s = | 0.38 | 5.03 | s = | 0.72 | 4.76 | s = | 0.42 | 4.34 | s = | 0.65 |
|  | D | 5.38 | $s_E=$ | 0.25 | 5.87 | $s_E=$ | 0.17 | 5.80 | $s_E=$ | 0.32 | 5.59 | $s_E=$ | 0.19 | 5.31 | $s_E=$ | 0.29 |
|  | E | 5.41 | | | 5.41 | | | 5.41 | | | 5.14 | | | 4.86 | | |
| 2 | A | 4.81 | | | 2.22 | | | 2.67 | | | 2.59 | | | 1.93 | | |
|  | B | 5.36 | x = | 5.02 | 3.12 | x = | 3.37 | 3.31 | x = | 3.49 | 3.25 | x = | 3.21 | 2.47 | x = | 2.66 |
|  | C | 4.69 | s = | 0.28 | 3.36 | s = | 0.78 | 3.43 | s = | 0.56 | 3.08 | s = | 0.45 | 2.87 | s = | 0.50 |
|  | D | 5.04 | $s_E=$ | 0.12 | 4.13 | $s_E=$ | 0.35 | 4.06 | $s_E=$ | 0.25 | 3.85 | $s_E=$ | 0.20 | 3.29 | $s_E=$ | 0.23 |
|  | E | 5.21 | | | 4.04 | | | 3.97 | | | 3.29 | | | 2.74 | | |
| 3 | A | 2.37 | | | 1.4. | | | 2.22 | | | 2.51 | | | 1.41 | | |
|  | B | 4.90 | x = | 4.43 | 2.53 | x = | 2.72 | 2.47 | x = | 2.62 | 2.34 | x = | 2.40 | 1.82 | x = | 1.62 |
|  | C | 4.55 | s = | 1.18 | 2.52 | s = | 0.94 | 2.38 | s = | 0.38 | 2.17 | s = | 0.15 | 1.40 | s = | 0.20 |
|  | D | 5.32 | $s_E=$ | 0.53 | 3.15 | $s_E=$ | 0.42 | 2.88 | $s_E=$ | 0.17 | 2.52 | $s_E=$ | 0.07 | 1.75 | $s_E=$ | 0.09 |
|  | E | 5.00 | | | 3.97 | | | 3.15 | | | 2.47 | | | 1.71 | | |
| 4 | A | 1.63 | | | 2.89 | | | 2.52 | | | 2.59 | | | 1.48 | | |
|  | B | 3.66 | x = | 3.91 | 2.14 | x = | 2.67 | 2.08 | x = | 2.25 | 1.95 | x = | 2.09 | 1.43 | x = | 1.42 |
|  | C | 4.13 | s = | 1.41 | 2.17 | s = | 0.50 | 1.89 | s = | 0.28 | 1.75 | s = | 0.31 | 1.12 | s = | 0.18 |
|  | D | 5.25 | $s_E=$ | 0.63 | 2.87 | $s_E=$ | 0.22 | 2.52 | $s_E=$ | 0.12 | 2.10 | $s_E=$ | 0.14 | 1.61 | $s_E=$ | 0.08 |
|  | E | 4.86 | | | 3.29 | | | 2.26 | | | 2.05 | | | 1.44 | | |
| 5 | A | 3.19 | | | 3.11 | | | 2.74 | | | 2.74 | | | 2.37 | | |
|  | B | 4.18 | x = | 4.39 | 4.35 | x = | 4.02 | 3.83 | x = | 3.63 | 3.44 | x = | 3.45 | 3.12 | x = | 2.90 |
|  | C | 4.55 | s = | 0.79 | 3.92 | s = | 0.55 | 3.64 | s = | 0.52 | 3.64 | s = | 0.41 | 2.80 | s = | 0.33 |
|  | D | 5.32 | $s_E=$ | 0.35 | 4.20 | $s_E=$ | 0.25 | 3.99 | $s_E=$ | 0.23 | 3.71 | $s_E=$ | 0.18 | 3.08 | $s_E=$ | 0.15 |
|  | E | 4.73 | | | 4.52 | | | 3.97 | | | 3.70 | | | 3.15 | | |
| 6 | A | 4.52 | | | 4.30 | | | 4.22 | | | 3.70 | | | 2.74 | | |
|  | B | 5.36 | x = | 5.20 | 5.39 | x = | 5.09 | 5.00 | x = | 4.86 | 4.61 | x = | 4.29 | 4.35 | x = | 3.60 |
|  | C | 4.76 | s = | 0.56 | 4.69 | s = | 0.56 | 4.83 | s = | 0.39 | 4.34 | s = | 0.35 | 3.50 | s = | 0.59 |
|  | D | 5.94 | $s_E=$ | 0.25 | 5.59 | $s_E=$ | 0.25 | 5.24 | $s_E=$ | 0.17 | 4.48 | $s_E=$ | 0.16 | 3.57 | $s_E=$ | 0.126 |
|  | E | 5.41 | | | 5.48 | | | 5.00 | | | 4.32 | | | 3.84 | | |

RESULT Table 5

Determination: HCO$_3$ (mM/L)

Donor and Mechanism Results, Mean, Standard Deviation, and Standard Error

Time of Storage

| Mech | Donor | Day 1 | | | Day 7 | | | Day 14 | | | Day 21 | | | Day 28 | | |
|---|---|---|---|---|---|---|---|---|---|---|---|---|---|---|---|---|
| 1 | A | 15.3 | | | 12.1 | | | 9.8 | | | 8.6 | | | 6.4 | | |
|  | B | 15.6 | x = | 15.8 | 14.3 | x = | 13.5 | 11.8 | x = | 11.6 | 10.3 | x = | 8.96 | 8.8 | x = | 7.24 |
|  | C | 15.1 | s = | 0.67 | 13.0 | s = | 0.96 | 11.8 | s = | 1.04 | 7.1 | s = | 1.23 | 6.9 | s = | 0.92 |
|  | D | 16.4 | $s_E=$ | 0.30 | 13.7 | $s_E=$ | 0.43 | 11.8 | $s_E=$ | 0.47 | 9.0 | $s_E=$ | 0.55 | 7.2 | $s_E=$ | 0.41 |
|  | E | 16.6 | | | 14.4 | | | 12.6 | | | 9.8 | | | 6.9 | | |
| 2 | A | 14.3 | | | 10.1 | | | 7.3 | | | 6.1 | | | 5.7 | | |
|  | B | 16.7 | x = | 15.5 | 12.6 | x = | 11.5 | 9.2 | x = | 9.12 | 7.2 | x = | 7.10 | 5.6 | x = | 5.72 |
|  | C | 14.9 | s = | 0.94 | 11.8 | s = | 0.97 | 10.2 | s = | 1.11 | 7.3 | s = | 0.60 | 5.9 | s = | 0.18 |
|  | D | 16.0 | $s_E=$ | 0.2 | 10.9 | $s_E=$ | 0.43 | 9.8 | $s_E=$ | 0.50 | 7.2 | $s_E=$ | 0.27 | 5.5 | $s_E=$ | 0.08 |
|  | E | 15.6 | | | 11.9 | | | 9.1 | | | 7.7 | | | 5.9 | | |
| 3 | A | 14.5 | | | 11.7 | | | 7.2 | | | 6.5 | | | 5.8 | | |
|  | B | 15.5 | x = | 14.9 | 11.8 | x = | 11.7 | 9.5 | x = | 8.88 | 7.8 | x = | 7.42 | 5.2 | x = | 5.56 |
|  | C | 14.3 | s = | 0.55 | 12.2 | s = | 0.55 | 9.5 | s = | 1.00 | 7.8 | s = | 0.55 | 5.5 | s = | 0.25 |
|  | D | 14.6 | $s_E=$ | 0.25 | 10.8 | $s_E=$ | 0.25 | 8.7 | $s_E=$ | 0.45 | 7.3 | $s_E=$ | 0.25 | 5.7 | $s_E=$ | 0.11 |
|  | E | 15.4 | | | 12.1 | | | 9.5 | | | 7.7 | | | 5.5 | | |
| 4 | A | 16.9 | | | 10.5 | | | 8.7 | | | 6.8 | | | 6.0 | | |
|  | B | 16.8 | x = | 16.5 | 10.8 | x = | 10.8 | 8.7 | x = | 8.64 | 7.3 | x = | 7.26 | 5.6 | x = | 5.88 |
|  | C | 15.5 | s = | 0.60 | 11.3 | s = | 0.33 | 8.8 | s = | 0.31 | 7.6 | s = | 0.32 | 5.7 | s = | 0.28 |
|  | D | 16.4 | $s_E=$ | 0.27 | 10.8 | $s_E=$ | 0.15 | 8.9 | $s_E=$ | 0.14 | 7.1 | $s_E=$ | 0.14 | 5.8 | $s_E=$ | 0.12 |
|  | E | 16.9 | | | 10.5 | | | 8.7 | | | 7.5 | | | 6.3 | | |
| 5 | A | 13.8 | | | 8.7 | | | 5.9 | | | 5.2 | | | 4.2 | | |
|  | B | 16.6 | x = | 15.4 | 11.2 | x = | 9.92 | 7.2 | x = | 7.04 | 5.5 | x = | 5.52 | 3.7 | x = | 3.84 |
|  | C | 15.1 | s = | 1.07 | 9.5 | s = | 1.01 | 7.5 | s = | 0.65 | 6.2 | s = 0.40 | 4.4 | s = | 0.44 | | |
|  | D | 15.5 | $s_E=$ | 0.48 | 9.5 | $s_E=$ | 0.45 | 7.3 | $s_E=$ | 0.29 | 5.4 | $s_E=$ | 0.18 | 3.5 | $s_E=$ | 0.20 |
|  | E | 16.1 | | | 10.7 | | | 7.3 | | | 5.3 | | | 3.4 | | |
| 6 | A | 9.8 | | | 5.9 | | | 4.1 | | | 3.0 | | | 2.3 | | |
|  | B | 12.0 | x = | 11.9 | 8.3 | x = | 7.96 | 6.9 | x = | 5.84 | 5.4 | x = | 4.52 | 3.7 | $xs_E=$ | 3.26 |
|  | C | 12.9 | s = | 1.38 | 8.7 | s = | 1.28 | 6.5 | s = | 1.14 | 5.0 | s = | 1.04 | 3.8 | s = | 0.71 |

RESULT Table 5-continued

Determination: $HCO_3$ (mM/L)

Donor and Mechanism Results, Mean, Standard Deviation, and Standard Error

| Mech | Donor | Day 1 | | Day 7 | | Day 14 | | Day 21 | | Day 28 | |
|---|---|---|---|---|---|---|---|---|---|---|---|
| | D | 13.3 | $s_E=$ 0.62 | 9.2 | $s_E=$ 0.57 | 6.4 | $s_E=$ 0.51 | 5.3 | $s_E=$ 0.46 | 3.8 | $s_E=$ 0.32 |
| | E | 11.4 | | 7.7 | | 5.3 | | 3.9 | | 2.7 | |

RESULT Table 6

Determination: $TCO_2$ (mM/L)

Donor and Mechanism Results, Mean, Standard Deviation, and Standard Error

| Mech | Donor | Day 1 | | Day 7 | | Day 14 | | Day 21 | | Day 28 | |
|---|---|---|---|---|---|---|---|---|---|---|---|
| 1 | A | 17.1 | — | 13.7 | — | 11.6 | — | 10.2 | — | 8.1 | — |
| | B | 17.4 | $x=$ 17.6 | 16.3 | $x=$ 15.3 | 14.1 | $x=$ 13.7 | 12.7 | $x=$ 12.3 | 11.4 | $x=$ 9.16 |
| | C | 16.8 | $s=$ 0.71 | 14.7 | $s=$ 1.16 | 13.9 | $s=$ 1.23 | 15.5 | $s=$ 2.05 | 8.6 | $s=$ 1.29 |
| | D | 18.1 | $s_E=$ 0.32 | 15.4 | $s_E=$ 0.52 | 13.8 | $s_E=$ 0.55 | 10.9 | $s_E=$ 0.91 | 9.0 | $s_E=$ 0.58 |
| | E | 18.5 | | 16.5 | | | | 12.12 | | 8.7 | |
| 2 | A | 15.7 | — | 11.2 | — | 8.0 | — | 6.9 | — | 6.6 | — |
| | B | 18.4 | $x=$ 16.9 | 14.0 | $x=$ 12.7 | 10.3 | $x=$ 10.2 | 8.1 | $x=$ 8.1 | 6.4 | $x=$ 6.56 |
| | C | 16.2 | $s=$ 1.05 | 13.2 | $s=$ 1.11 | 11.5 | $s=$ 1.33 | 8.6 | $s=$ 0.74 | 6.8 | $s=$ 0.17 |
| | D | 17.3 | $s_E=$ 0.47 | 12.0 | $s_E=$ 0.50 | 10.9 | $s_E=$ 0.59 | 8.2 | $s_E=$ 0.33 | 6.4 | $s_E=$ 0.07 |
| | E | 17.1 | | 13.2 | | 10.2 | | 8.8 | | 6.6 | |
| 3 | A | 15.3 | — | 12.7 | — | 7.8 | — | 7.1 | — | 6.3 | — |
| | B | 16.7 | $x=$ 15.9 | 12.8 | $x=$ 12.8 | 10.5 | $x=$ 9.74 | 8.7 | $x=$ 8.1 | 5.8 | $x=$ 6.12 |
| | C | 15.3 | $s=$ 0.71 | 13.3 | $s=$ 0.70 | 10.4 | $s=$ 1.16 | 8.5 | $s=$ 0.64 | 6.1 | $s=$ 0.24 |
| | D | 15.7 | $s_E=$ 0.2 | 11.7 | $s_E=$ 0.1 | 9.5 | $s_E=$ 0.52 | 8.0 | $s_E=$ 0.28 | 6.4 | $s_E=$ 0.11 |
| | E | 16.7 | | 13.5 | | 10.5 | | 8.4 | | 6.0 | |
| 4 | A | 17.9 | — | 11.5 | — | 8.9 | — | 7.4 | — | 6.5 | — |
| | B | 17.8 | $x=$ 17.5 | 11.5 | $x=$ 11.6 | 9.5 | $x=$ 9.30 | 7.9 | $x=$ 7.78 | 6.1 | $x=$ 6.22 |
| | C | 16.4 | $s=$ 0.70 | 12.1 | $s=$ 0.28 | 9.4 | $s=$ 0.26 | 8.1 | $s=$ 0.28 | 6.1 | $s=$ 0.16 |
| | D | 17.4 | $s_E=$ 0.31 | 11.7 | $s_E=$ 0.13 | 9.5 | $s_E=$ 0.11 | 7.6 | $s_E=$ 0.12 | 6.2 | $s_E=$ 0.07 |
| | E | 18.2 | | 11.4 | | 9.2 | | 7.9 | | 6.2 | |
| 5 | A | 14.9 | — | 9.5 | — | 6.6 | — | 5.8 | — | 4.8 | — |
| | B | 18.2 | $x=$ 16.7 | 12.4 | $x=$ 10.9 | 8.1 | $x=$ 7.84 | 6.2 | $x=$ 6.26 | 4.2 | $x=$ 4.44 |
| | C | 16.4 | $s=$ 1.25 | 10.5 | $s=$ 1.20 | 8.3 | $s=$ 0.70 | 7.1 | $s=$ 0.50 | 5.2 | $s=$ 0.54 |
| | D | 16.7 | $s_E=$ 0.56 | 10.3 | $s_E=$ 0.54 | 8.0 | $s_E=$ 0.31 | 6.2 | $s_E=$ 0.22 | 4.1 | $s_E=$ 0.24 |
| | E | 17.5 | | 11.9 | | 8.2 | | 6.0 | | 3.9 | |
| 6 | A | 11.7 | — | 7.1 | — | 5.0 | — | 3.9 | — | 3.2 | — |
| | B | 13.8 | $x=$ 14.0 | 10.0 | $x=$ 9.54 | 8.8 | $x=$ 7.32 | 6.9 | $x=$ 5.80 | 5.0 | $x=$ 4.40 |
| | C | 14.7 | $s=$ 1.48 | 10.3 | $s=$ 1.47 | 8.1 | $s=$ 1.48 | 6.4 | $s=$ 1.27 | 5.1 | $s=$ 0.93 |
| | D | 15.7 | $s_E=$ 0.66 | 10.9 | $s_E=$ 0.66 | 7.9 | $s_E=$ 0.66 | 6.7 | $s_E=$ 0.57 | 5.1 | $s_E=$ 0.41 |
| | E | 13.9 | | 9.4 | | 6.8 | | 5.1 | | 3.6 | |

RESULTS TABLE 7

Determination: $Na^+$ (mEq/L)

Donor and Mechanism Results, Mean, Standard Deviation, and Standard Error

| Mech | Donor | Day 1 | | Day 7 | | Day 14 | | Day 21 | | Day 28 | |
|---|---|---|---|---|---|---|---|---|---|---|---|
| 1 | A | 179 | — | 173 | — | 168 | — | 173 | — | 167 | — |
| | B | 187 | $x=$ 184.2 | 183 | $x=$ 178.6 | 175 | $x=$ 172 | 174 | $x=$ 173.76 | 168 | $x=$ 169.2 |
| | C | 183 | $s=$ 3.35 | 179 | $s=$ 3.65 | 175 | $s=$ 3.08 | 172 | $s=$ 1.14 | 172 | $s=$ 2.59 |
| | D | 185 | $s_E=$ | | $s_E=$ 1.63 | 170 | $s_E=$ 1.38 | 174 | $s_E=$ 0.51 | 167 | $s_E=$ 1.16 |
| | E | 187 | | 180 | | 172 | | 175 | | 172 | |
| 2 | A | 183 | — | 159 | — | 148 | — | 142 | — | 141 | — |
| | B | 187 | $x=$ 183.6 | 168 | $x=$ 164.6 | 161 | $x=$ 155.2 | 157 | $x=$ 153.6 | 143 | $x=$ 145.6 |
| | C | 181 | $s=$ 167 | $s=$ | 158 | $s=$ 3.91 | 159 | $s=$ 4.97 | 153 | $s=$ 6.84 | 153 | $s=$ 4.56 |
| | D | 183 | $s_E=$ 0.98 | 162 | $s_E=$ 1.75 | 156 | $s_E=$ 2.22 | 153 | $s_E=$ 3.06 | 146 | $s_E=$ 2.04 |
| | E | 184 | | 167 | | 153 | | 157 | | 145 | |
| 3 | A | 176 | — | 157 | — | 144 | — | 134 | — | 133 | — |
| | B | 187 | $x=$ 183.8 | 170 | $x=$ 163.40 | 162 | $x=$ 155 | 149 | $x=$ 143.6 | 143 | $x=$ 142.6 |
| | C | 187 | $s=$ 4.87 | 163 | $s=$ 4.62 | 157 | $s=$ 6.78 | 146 | $s=$ 5.77 | 146 | $s=$ 5.50 |
| | D | 182 | $s_E=$ 2.18 | 163 | $s_E=$ 2.06 | 158 | $s_E=$ 3.03 | 146 | $s_E=$ 2.58 | 146 | $s_E=$ 2.46 |
| | E | 187 | | 164 | | 154 | | 143 | | 145 | |
| 4 | A | 178 | — | 156 | — | 144 | — | 133 | — | 130 | — |
| | B | 185 | $x=$ 183.2 | 167 | $x=$ 162.0 | 155 | $x=$ 149 | 144 | $x=$ 142.6 | 142 | $x=$ 137.0 |
| | C | 184 | $s=$ 3.11 | 163 | $s=$ 4.18 | 154 | $s=$ 5.29 | 150 | $s=$ 6.47 | 140 | $s=$ 4.69 |
| | D | 183 | $s_E=$ 1.39 | 164 | $s_E=$ 1.87 | 148 | $s_E=$ 2.37 | 146 | $s_E=$ 2.89 | 138 | $s_E=$ 2.10 |
| | E | 186 | | 160 | | 144 | | 140 | | 135 | |
| 5 | A | 183 | — | 162 | — | 164 | — | 161 | — | 156 | — |
| | B | 191 | $x=$ 185.8 | 176 | $x=$ 170.4 | 173 | $x=$ 168.4 | 168 | $x=$ 163.8 | 165 | $x=$ 161 |
| | C | 183 | $s=$ 3.35 | 172 | $s=$ 5.13 | 172 | $s=$ 4.04 | 165 | $s=$ 3.27 | 163 | $s=$ 3.81 |
| | D | 187 | $s_E=$ 1.50 | 171 | $s_E=$ 2.29 | 165 | $s_E=$ 1.81 | 160 | $s_E=$ 1.6 | 163 | $s_E=$ 1.70 |
| | E | 185 | | 171 | | 168 | | 165 | | 158 | |
| 6 | A | 161 | — | 149 | — | 137 | — | 119 | — | 108 | — |
| | B | 178 | $x=$ 170.6 | 167 | $x=$ 161.4 | 164 | $x=$ 151.6 | 151 | $x=$ 139.4 | 140 | $x=$ 129.8 |
| | C | 173 | $s=$ 6.27 | 164 | $s=$ 7.16 | 153 | $s=$ 9.84 | 143 | $s=$ 12.0 | 137 | $s=$ 12.83 |
| | D | 169 | $s_E=$ 2.80 | 162 | $s_E=$ 3.20 | 149 | $s_E=$ 4.40 | 142 | $s_E=$ 5.37 | 135 | $s_E=$ 5.74 |
| | E | 172 | | 165 | | 155 | | 142 | | 129 | |

RESULTS TABLE 8

Determination: $K^+$ (mEq/L)  
Donor and Mechanism Results, Mean, Standard Deviation, and Standard Error

| Mech | Donor | Day 1 | | | Day 7 | | | Day 14 | | | Day 21 | | | Day 28 | | |
|---|---|---|---|---|---|---|---|---|---|---|---|---|---|---|---|---|
| 1 | A | 5.3 | | | 12.5 | | | 16.7 | | | 10.7 | | | 13.5 | | |
|  | B | 6.4 | $x=$ | 5.72 | 15.6 | $x=$ | 13.96 | 11.6 | $x=$ | 16.68 | 13.8 | $x=$ | 12.30 | 13.8 | $x=$ | 13.74 |
|  | C | 6.0 | $s=$ | 0.56 | 13.9 | $s=$ | 1.11 | 18.3 | $s=$ | 2.93 | 12.0 | $s=$ | 1.17 | 13.8 | $s=$ | 0.13 |
|  | D | 5.0 | $s_E=$ | 0.25 | 13.7 | $s_E=$ | 0.50 | 18.2 | $s_E=$ | 1.31 | 12.0 | $s_E=$ | 0.52 | 13.8 | $s_E=$ | 0.06 |
|  | E | 5.9 | | | 14.1 | | | 18.6 | | | 13.0 | | | 13.8 | | |
| 2 | A | 6.5 | | | 13.3 | | | 13.7 | | | 13.8 | | | 13.8 | | |
|  | B | 7.2 | $x=$ | 6.64 | 12.7 | $x=$ | 12.56 | 13.8 | $x=$ | 13.78 | 13.8 | $x=$ | 13.8 | 15.8 | $x=$ | 14.18 |
|  | C | 7.0 | $s=$ | 0.59 | 12.8 | $s=$ | 0.58 | 13.7 | $s=$ | 0.04 | 13.8 | $s=$ | 0.00 | 13.7 | $s=$ | 0.91 |
|  | D | 5.7 | $s_E=$ | 0.26 | 11.8 | $s_E=$ | 0.26 | 13.8 | $s_E=$ | 0.02 | 13.8 | $s_E=$ | 0.00 | 13.8 | $s_E=$ | 0.41 |
|  | E | 6.8 | | | 12.2 | | | 13.8 | | | 13.8 | | | 13.8 | | |
| 3 | A | 6.1 | | | 13.7 | | | 13.8 | | | 13.8 | | | 13.8 | | |
|  | B | 8.6 | $x=$ | 7.30 | 13.7 | $x=$ | 13.70 | 13.8 | $x=$ | 13.8 | 13.8 | $x=$ | 13.8 | 13.8 | $x=$ | 13.8 |
|  | C | 7.8 | $s=$ | 0.95 | 13.7 | $s=$ | 0.00 | 13.8 | $s=$ | 0.00 | 13.8 | $s=$ | 0.00 | 13.8 | $s=$ | 0.00 |
|  | D | 6.9 | $s_E=$ | 0.42 | 13.7 | $s_E=$ | 0.00 | 13.8 | $s_E=$ | 0.00 | 13.8 | $s_E=$ | 0.00 | | | |
|  | E | 7.1 | | | 13.7 | | | 13.8 | | | 13.8 | | | 13.8 | | |
| 4 | A | 5.2 | | | 13.7 | | | 13.8 | | | 13.8 | | | 13.8 | | |
|  | B | 9.7 | $x=$ | 7.80 | 13.7 | $x=$ | 13.74 | 13.8 | $x=$ | 13.8 | 13.8 | $x=$ | 13.8 | 13.8 | $x=$ | 13.8 |
|  | C | 8.6 | $s=$ | 1.66 | 13.7 | $s=$ | 0.05 | 13.8 | $s=$ | 0.00 | 13.8 | $s=$ | 0.00 | 13.8 | $s=$ | 0.00 |
|  | D | 7.6 | $s_E=$ | 0.74 | 13.8 | $s_E=$ | 0.02 | 13.8 | $s_E=$ | 0.00 | 13.8 | $s_E=$ | 0.00 | 13.8 | $s_E=$ | 0.00 |
|  | E | 7.9 | | | 13.8 | | | 13.8 | | | 13.8 | | | 13.8 | | |
| 5 | A | 5.8 | | | 11.2 | | | 13.7 | | | 13.8 | | | 13.8 | | |
|  | B | 6.6 | $x=$ | 6.0 | 19.8 | $x=$ | 16.48 | 13.8 | $x=$ | 13.50 | 13.8 | $x=$ | 13.8 | 13.8 | $x=$ | 13.8 |
|  | C | 6.2 | $s=$ | 0.42 | 17.2 | $s=$ | 3.18 | 13.8 | $s=$ | 0.62 | 13.8 | $s=$ | 0.00 | 13.8 | $s=$ | 0.00 |
|  | D | 5.5 | $s_E=$ | 0.19 | 17.5 | $s_E=$ | 1.42 | 13.8 | $s_E=$ | 0.28 | 13.8 | $s_E=$ | 0.00 | 13.8 | $s_E=$ | 0.00 |
|  | E | 5.9 | | | 16.7 | | | 12.4 | | | 13.8 | | | 13.8 | | |
| 6 | A | 5.9 | | | 11.9 | | | 16.8 | | | 19.9 | | | 11.1 | | |
|  | B | 7.0 | $x=$ | 6.30 | 13.6 | $x=$ | 12.26 | 19.1 | $x=$ | 16.76 | 12.2 | $x=$ | 18.02 | 13.8 | $x=$ | 12.24 |
|  | C | 6.6 | $s=$ | 0.56 | 12.6 | $s=$ | 0.85 | 15.9 | $s=$ | 1.40 | 19.2 | $s=$ | 3.26 | 11.9 | $s=$ | 1.17 |
|  | D | 5.6 | $s_E=$ | 0.25 | 11.6 | $s_E=$ | 0.38 | 15.5 | $s_E=$ | 0.63 | 19.3 | $s_E=$ | 1.46 | 11.3 | $s_E=$ | 0.52 |
|  | E | 6.4 | | | 11.6 | | | 16.5 | | | 19.5 | | | 13.1 | | |

RESULTS TABLE 9

Determination: $PCO_2$ (mmHg)  
Donor and Mechanism Results, Mean, Standard Deviation, and Standard Error

| Mech | Donor | Day 1 | | | Day 7 | | | Day 14 | | | Day 12 | | | Day 28 | | |
|---|---|---|---|---|---|---|---|---|---|---|---|---|---|---|---|---|
| 1 | A | 54.9 | | | 51.0 | | | 53.9 | | | 52.2 | | | 52.1 | | |
|  | B | 54.6 | $x=$ | 55.7 | 66.1 | $x=$ | 58.56 | 70.0 | $x=$ | 64.8 | 74.1 | $x=$ | 62.46 | 58.8 | $x=$ | 54.96 |
|  | C | 53.2 | $s=$ | 4.24 | 54.1 | $s=$ | 7.23 | 65.1 | $s=$ | 7.59 | 54.2 | $s=$ | 10.18 | 53.0 | $s=$ | 2.69 |
|  | D | 52.7 | $s_E=$ | 1.90 | 55.1 | $s_E=$ | 3.23 | 61.6 | $s_E=$ | 3.39 | 59.5 | $s_E=$ | 4.55 | 56.4 | $s_E=$ | 1.21 |
|  | E | 63.1 | | | 66.5 | | | 73.4 | | | 72.3 | | | 54.5 | | |
| 2 | A | 41.0 | | | 33.5 | | | 21.5 | | | 22.5 | | | 26.0 | | |
|  | B | 53.1 | $x=$ | 44.22 | 45.2 | $x=$ | 39.16 | 31.9 | $x=$ | 31.36 | 25.1 | $x=$ | 28.44 | 20.9 | $x=$ | 23.54 |
|  | C | 40.3 | $s=$ | 5.24 | 42.4 | $s=$ | 5.33 | 38.9 | $s=$ | 6.35 | 33.9 | $s=$ | 4.58 | 25.6 | $s=$ | 2.60 |
|  | D | 42.0 | $s_E=$ | 2.34 | 33.6 | $s_E=$ | 2.38 | 33.9 | $s_E=$ | 2.84 | 30.8 | $s_E=$ | 2.05 | 24.6 | $s_E=$ | 1.16 |
|  | E | 44.7 | | | 41.1 | | | 30.6 | | | 29.9 | | | 20.6 | | |
| 3 | A | 28.3 | | | 29.9 | | | 18.5 | | | 17.5 | | | 13.8 | | |
|  | B | 33.9 | $x=$ | 33.22 | 31.5 | $x=$ | 32.42 | 27.4 | $x=$ | 24.48 | 26.1 | $x=$ | 21.06 | 15.2 | $x=$ | 14.82 |
|  | C | 31.2 | $s=$ | 4.60 | 33.6 | $s=$ | 4.20 | 27.1 | $s=$ | 3.93 | 21.5 | $s=$ | 3.34 | 14.1 | $s=$ | 1.39 |
|  | D | 32.1 | $s_E=$ | 2.06 | 28. | $s_E=$ | 1.88 | 22.4 | $s_E=$ | 1.76 | 21.6 | $s_E=$ | 1.49 | 17.1 | $s_E=$ | 0.62 |
|  | E | 40.6 | | | 39.0 | | | 27.0 | | | 18.6 | | | 13.9 | | |
| 4 | A | 33.5 | | | 30.6 | | | 23.2 | | | 17.2 | | | 13.6 | | |
|  | B | 30.0 | $x=$ | 32.88 | 22.5 | $x=$ | 25.92 | 22.5 | $x=$ | 18.66 | 16.3 | $x=$ | 14.18 | 13.1 | $x=$ | 10.38 |
|  | C | 27.9 | $s=$ | 6.53 | 25.5 | $s=$ | 5.28 | 17.7 | $s=$ | 3.17 | 12.6 | $s=$ | 2.37 | 7.1 | $s=$ | 2.37 |
|  | D | 31.8 | $s_E=$ | 2.92 | 26.7 | $s_E=$ | 2.36 | 15.6 | $s_E=$ | 1.42 | 13.4 | $s_E=$ | 1.06 | 10.1 | $s_E=$ | 1.06 |
|  | E | 41.2 | | | 24.3 | | | 14.3 | | | 11.4 | | | 8.0 | | |
| 5 | A | 30.9 | | | 24.1 | | | 18.4 | | | 18.2 | | | 17.4 | | |
|  | B | 47.7 | $x=$ | 40.40 | 35.2 | $x=$ | 29.34 | 25.2 | $x=$ | 23.74 | 20.6 | $x=$ | 21.10 | 15.6 | $x=$ | 16.54 |
|  | C | 41.3 | $s=$ | 6.53 | 27.2 | $s=$ | 5.28 | 25.3 | $s=$ | 3.17 | 24.8 | $s=$ | 2.37 | 20.2 | $s=$ | 2.37 |
|  | D | 37.5 | $s_E=$ | 2.92 | 25.4 | $s_E=$ | 2.36 | 23.4 | $s_E=$ | 1.42 | 20.9 | $s_E=$ | 1.06 | 15.5 | $s_E=$ | 1.06 |
|  | E | 44.6 | | | 34.8 | | | 26.4 | | | 21.0 | | | 14.0 | | |
| 6 | A | 57.2 | | | 35.3 | | | 27.7 | | | 26.3 | | | 24.4 | | |
|  | B | 55.9 | $x=$ | 64.68 | 50.5 | $x=$ | 46.60 | 54.7 | $x=$ | 43.96 | 46.5 | $x=$ | 38.16 | 37.7 | $x=$ | 32.74 |
|  | C | 56.5 | $s=$ | 11.17 | 43.2 | $s=$ | 7.31 | 46.3 | $s=$ | 9.89 | 43.2 | $s=$ | 8.35 | 37.7 | $s=$ | 6.03 |
|  | D | 76.4 | $s_E=$ | 5.00 | 51.4 | $s_E=$ | 3.27 | 46.1 | $s_E=$ | 4.42 | 42.0 | $s_E=$ | 3.74 | 35.5 | $s_E=$ | 2.69 |
|  | E | 77.4 | | | 52.6 | | | 45.0 | | | 32.8 | | | 28.4 | | |

RESULTS Table 10

Determination: $PO_2$ (mmHg)  
Donor and Mechanism Results, Mean, Standard Deviation, and Standard Error

| Mech | Donor | Day 1 | | | Day 7 | | | Day 14 | | | Day 21 | | | Day 28 | | |
|---|---|---|---|---|---|---|---|---|---|---|---|---|---|---|---|---|
| 1 | A | 66.4 | | | 66.5 | | | 83.3 | | | 173.4 | | | 222.0 | | |
|  | B | 54.7 | $x=$ | 50.64 | 42.2 | $x=$ | 55.10 | 54.8 | $x=$ | 70.2 | 70.2 | $x=$ | 136.48 | 171.2 | $x=$ | 200.00 |
|  | C | 47.7 | $s=$ | 10.28 | 57.5 | $s=$ | 9.35 | 74.5 | $s=$ | 10.90 | 192.5 | $s=$ | 49.07 | 206.9 | $s=$ | 18.72 |
|  | D | 44.0 | $s_E=$ | 4.60 | 59.5 | $s_E=$ | 4.18 | 74.0 | $s_E=$ | 4.88 | 137.0 | $s_E=$ | 21.95 | 195.5 | $s_E=$ | 8.37 |
|  | E | 40.4 | | | 47.8 | | | 64.4 | | | 109.3 | | | 204.6 | | |
| 2 | A | 42.4 | | | 77.7 | | | 194.5 | | | 209.8 | | | 167.1 | | |
|  | B | 30.1 | $x=$ | 41.08 | 34.5 | $x=$ | 54.86 | 64.5 | $x=$ | 110.0 | 109.8 | $x=$ | 136.50 | 114.8 | $x=$ | 172.42 |
|  | C | 43.3 | $s=$ | 6.26 | 43.2 | $s=$ | 19.53 | 89.5 | $s=$ | 49.53 | 101.7 | $s=$ | 54.76 | 160.4 | $s=$ | 39.95 |
|  | D | 43.8 | $s_E=$ | 2.80 | 73.8 | $s_E=$ | 8.74 | 98.3 | $s_E=$ | 22.16 | 178.7 | $s_E=$ | 24.49 | 216.3 | $s_E=$ | 17.87 |

RESULTS Table 10-continued

Determination: PO₂ (mmHg)  
Donor and Mechanism Results, Mean, Standard Deviation, and Standard Error

| Mech | Donor | Day 1 | | | Day 7 | | | Day 14 | | | Day 21 | | | Day 28 | | |
|---|---|---|---|---|---|---|---|---|---|---|---|---|---|---|---|---|
| 3 | E | 45.8 | | | 45.1 | | | 103.2 | | | 82.5 | | | 203.5 | | |
|   | A | 45.8 | | | 40.2 | | | 79.2 | | | 110.4 | | | 74.6 | | |
|   | B | 32.5 | $x=$ | 41.46 | 41.2 | $x=$ | 46.04 | 66.3 | $x=$ | 95.88 | 199.7 | $x=$ | 177.60 | | | |
|   | C | 42.4 | $s=$ | 5.34 | 48.6 | $s=$ | 5.42 | 105.1 | $s=$ | 18.15 | 70.5 | $s=$ | 38.69 | 202.6 | $s=$ | 57.67 |
|   | D | 45.2 | $s_E=$ | 2.39 | 53.3 | $s_E=$ | 2.42 | 104.5 | $s_E=$ | 8.2 | 157.6 | $s_E=$ | 17.30 | 208.4 | $s_E=$ | 25.79 |
|   | E | 41.4 | | | 46.9 | | | 72.7 | | | 74.3 | | | 202.7 | | |
|   | A | 70.0 | | | 50.5 | | | 62.2 | | | 68.3 | | | 68.6 | | |
| 4 | B | 27.2 | $x=$ | 44.14 | 38.9 | $x=$ | 37.63 | 56.1 | $x=$ | 59.54 | 57.5 | $x=$ | 73.42 | 157.3 | $x=$ | 160.94 |
|   | C | 42.2 | $s=$ | 15.73 | 42.7 | $s=$ | 18.99 | 60.0 | $s=$ | 4.28 | 45.8 | $s=$ | 29.67 | 194.4 | $s=$ | 54.61 |
|   | D | 42.4 | $s_E=$ | 7.04 | 53.0 | $s_E=$ | 8.49 | 64.9 | $s_E=$ | 1.91 | 123.2 | $s_E=$ | 13.27 | 179.6 | $s_E=$ | 24.42 |
|   | E | 38.9 | | | 48.5 | | | 54.5 | | | 72.3 | | | 204.7 | | |
|   | A | 49.4 | | | 62.9 | | | 146.6 | | | 234.9 | | | 198.8 | | |
| 5 | B | 32.3 | $x=$ | 41.26 | 44.3 | $x=$ | 57.08 | 105.6 | $x=$ | 119.58 | 116.7 | $x=$ | 153.58 | 207.9 | $x=$ | 172.22 |
|   | C | 42.5 | $s=$ | 6.17 | 60.7 | $s=$ | 10.83 | 118.6 | $s=$ | 22.50 | 125.7 | $s=$ | 60.71 | 151.7 | $s=$ | 29.31 |
|   | D | 42.5 | $s_E=$ | 2.76 | 70.0 | $s_E=$ | 4.84 | 136.2 | $s_E=$ | 10.06 | 199.4 | $s_E=$ | 27.15 | 160.4 | $s_E=$ | 13.11 |
|   | E | 39.6 | | | 47.5 | | | 90.9 | | | 91.2 | | | 142.3 | | |
|   | A | 63.3 | | | 83.7 | | | 217.5 | | | 230.9 | | | 180.1 | | |
| 6 | B | 43.3 | $x=$ | 54.64 | 51.4 | $x=$ | 66.06 | 71.5 | $x=$ | 157.32 | 66.8 | $x=$ | 130.78 | 101.4 | $x=$ | 175.50 |
|   | C | 53.8 | $s=$ | 7.36 | 65.4 | $s=$ | 11.54 | 242.7 | $s=$ | 71.83 | 113.1 | $s=$ | 61.43 | 191.2 | $s=$ | 42.80 |
|   | D | 54.6 | $s_E=$ | 3.29 | 66.2 | $s_E=$ | 5.16 | 144.4 | $s_E=$ | 32.12 | 137.3 | $s_E=$ | 27.47 | 194.6 | $s_E=$S | 19.14 |
|   | E | 58.2 | | | 63.6 | | | 110.5 | | | 105.8 | | | 210.2 | | |

STATISTICS TABLE 1

TWO WAY ANALYSIS OF VARIANCE FOR pH

DONOR SUMS

| MECH | DAYS OF STORAGE | | | | | Mesh Σ | Mech X̄ | Dunnett's Test t-Value |
|---|---|---|---|---|---|---|---|---|
|  | 1 | 7 | 14 | 21 | 28 | | | |
| 1 | 35.342 | 34.888 | 34.349 | 33.950 | 33.642 | 172.171 | 6.89 | |
| 2 | 35.812 | 35.413 | 35.391 | 35.083 | 35.003 | 176.702 | 7.07 | 12.8 |
| 3 | 36.337 | 35.878 | 358.78 | 35.816 | 35.932 | 179.841 | 7.19 | 21.8 |
| 4 | 36.593 | 36.170 | 36.437 | 36.633 | 36.841 | 182.674 | 7.31 | 29.8 |
| 5 | 36.006 | 35.741 | 35.430 | 35.170 | 34.884 | 177.231 | 7.09 | 14.4 |
| 6 | 34.417 | 34.240 | 33.713 | 33.434 | 33.046 | 168.860 | 6.75 | −9.4 |
| TIME Σ | 214.51 | 212.33 | 211.20 | 210.09 | 209.35 | | | |

ANOVA TABLE 1

| SOURCE | SUM OF SQUARES | DEGREES OF FREEDOM | MEAN SQUARE | F VALUE |
|---|---|---|---|---|
| Mech | 5.069 | 5 | 1.014 | 405.60* |
| Time | .54842 | 4 | 0.137 | 54.80* |
| Interaction | .414 | 20 | 0.021 | 8.40* |
| Error | .29996 | 120 | 0.0025 | |
| Total | 6.331 | 149 | | |

DONOR SUM OF SQUARES = 6.031  
INTERACTION SS = DONOR SS - MECH SS - TIME SS  
*DENOES SIGNIFICANCE

STATISTICS TABLE 2

TWO WAY ANALYSIS OF VARIANCE FOR GLUCOSE (MG/DL)

DONOR SUMS

| Mech | DAYS OF STORAGE | | | | | Mech Σ | Mech X̄ | Dunnett's Test t-Value |
|---|---|---|---|---|---|---|---|---|
|  | 1 | 7 | 14 | 21 | 28 | | | |
| 1 | 1760 | 1607 | 1338 | 1145 | 928 | 6,778 | 271.12 | |
| 2 | 1713 | 1138 | 1144 | 795 | 606 | 5,396 | 215.84 | −11.44 |
| 3 | 1677 | 1309 | 1007 | 716 | 417 | 5,126 | 205.04 | −13.68 |
| 4 | 1744 | 1284 | 910 | 635 | 384 | 4,957 | 198.28 | −15.08 |
| 5 | 1542 | 1178 | 849 | 548 | 322 | 4,439 | 177.56 | −19.37 |
| 6 | 1719 | 1601 | 1351 | 1231 | 1070 | 6,972 | 278.88 | + 1.61 |
| Time Σ | 10155 | 8117 | 6599 | 5070 | 3727 | | | |

ANOVA TABLE 2

| SOURCE | SUM OF SQUARES | DEGREES OF FREEDOM | MEAN SQUARE | F VALUE |
|---|---|---|---|---|
| Mech | 211,878 | 5 | 42375.6 | 145.29* |
| Time | 848,170 | 4 | 212042.5 | 726.99* |
| Interacton | 56,887 | 20 | 2844.4 | 9.75* |
| Error | 35,000 | 120 | 291.67 | |
| Total | 1,151,935.0 | 149 | | |

DONOR SUM OF SQUARES = 1,116,935  
INTERACTION SS = DONOR SS - MECH SS - TIME SS  
*DENOTES SIGNIFICANCE

STATISTICS TABLE 3
TWO WAY ANALYSIS OF VARIANCE FOR 2,3DPG (μM/gHb)

DONOR SUMS

| Mech | DAYS OF STORGE | | | | | Mech Σ | MECH X̄ | Dunnett's Test t-Value |
|---|---|---|---|---|---|---|---|---|
| | 1 | 7 | 14 | 21 | 28 | | | |
| 1 | 63.99 | 43.25 | 14.70 | 3.790 | 2.060 | 127.79 | 5.11 | |
| 2 | 69.27 | 60.91 | 79.39 | 8.084 | 68.59 | 359.00 | 14.36 | 20.8 |
| 3 | 67.14 | 57.21 | 81.82 | 86.71 | 68.56 | 361.44 | 14.96 | 21.0 |
| 4 | 63.76 | 62.41 | 79.31 | 79.20 | 64.88 | 349.56 | 13.98 | 19.9 |
| 5 | 63.02 | 66.17 | 82.44 | 83.58 | 77.09 | 372.30 | 14.89 | 22.0 |
| 6 | 64.65 | 23.44 | 10.88 | 14.62 | 65.23 | 128.82 | 5.15 | 0.1 |
| Time Σ | 391.83 | 313.39 | 348.54 | 348.74 | 296.41 | | | |

ANOVA TABLE 3

| SOURCE | SUM OF SQUARES | DEGREES OF FREEDOM | MEAN SQUARE | F VALUE |
|---|---|---|---|---|
| Mech | 2,887.80 | 5 | 577.56 | 232.89* |
| Time | 181.45 | 4 | 45.36 | 18.29* |
| Interaction | 1,097.75 | 20 | 54.89 | 22.13* |
| Error | 297.61 | 120 | 2.48 | |
| Total | 4,465.00 | 149 | | |

DONOR SUM OF SQUARES = 4,167.00
INTERACTION SS = DONOR SS - MECH SS - TIME SS
*DENOTES SIGNIFICANCE

TABLE 4
STATISTICS
TWO WAY ANALYSIS OF VARIANCE FOR ATP (μM/gHb)

DONOR SUMS

| Mech | DAYS OF STORAGE | | | | | Mech Σ | Mech X̄ | Dunnett's Test t-Value |
|---|---|---|---|---|---|---|---|---|
| | 1 | 7 | 14 | 21 | 28 | | | |
| 1 | 26.02 | 26.79 | 26.36 | 25.27 | 23.55 | 127.99 | 5.12 | |
| 2 | 25.11 | 16.87 | 17.44 | 16.06 | 13.30 | 88.78 | 3.55 | − 9.25 |
| 3 | 22.14 | 13.58 | 13.10 | 12.01 | 8.09 | 68.92 | 2.76 | −13.90 |
| 4 | 19.53 | 13.36 | 11.27 | 10.44 | 7.08 | 61.68 | 2.47 | −15.61 |
| 5 | 21.97 | 20.10 | 18.17 | 17.23 | 14.52 | 91.99 | 3.68 | − 8.48 |
| 6 | 25.99 | 25.45 | 24.29 | 21.45 | 18.00 | 115.18 | 4.61 | − 3.00 |
| Time Σ | 140.76 | 116.15 | 110.63 | 102.46 | 84.54 | | | |

ANOVA TABLE 4

| SOURCE | SUM OF SQUARES | DEGREES OF FREEDOM | MEAN SQUARE | F VALUE |
|---|---|---|---|---|
| Mech | 131.75 | 5 | 26.35 | 73.81* |
| Time | 56.18 | 4 | 14.05 | 39.36* |
| Interaction | 14.10 | 20 | 0.71 | 1.99* |
| Error | 42.868 | 120 | 0.36 | |
| Total | 244.89 | 149 | | |

DONOR SUM OF SQUARES = 202.03
INTERACTION SS = DONOR SS - MECH SS - TIME SS
*DENOES SIGNIFICANCE

TABLE 5
STATISTICS
TWO WAY ANALYSIS OF VARIANCE FOR HCO₃ (mM/L)

DONOR SUMS

| MECH | DAYS OF STORAGE | | | | | MECH Σ | MECH X̄ | Dunnett's Test t-Value |
|---|---|---|---|---|---|---|---|---|
| | 1 | 7 | 14 | 21 | 28 | | | |
| 1 | 79.00 | 67.50 | 57.80 | 44.80 | 36.20 | 285.30 | 11.41 | − 7.04 |
| 2 | 77.50 | 57.30 | 45.60 | 35.50 | 28.60 | 244.50 | 9.78 | |
| 3 | 74.30 | 58.60 | 44.40 | 37.10 | 27.70 | 242.10 | 9.68 | − 7.47 |
| 4 | 82.50 | 53.90 | 43.80 | 36.30 | 29.40 | 245.90 | 9.84 | − 6.78 |
| 5 | 77.10 | 49.60 | 35.20 | 27.60 | 19.20 | 208.70 | 8.35 | −13.22 |
| 6 | 59.40 | 39.80 | 29.20 | 22.60 | 16.30 | 167.30 | 6.69 | −20.39 |
| TIME Σ | 449.80 | 326.70 | 256.00 | 203.90 | 157.40 | | | |

ANOVA TABLE 5

| Source | Sum of Squares | Degrees of Freedom | Mean Square | F Value |
|---|---|---|---|---|
| Mech | 320.83 | 5 | 64.17 | 95.78* |
| Time | 1746.77 | 4 | 436.69 | 651.78* |
| Interaction | 41.14 | 20 | 2.06 | 3.07* |
| Error | 80.95 | 120 | 0.67 | |

TABLE 5-continued
STATISTICS
TWO WAY ANALYSIS OF VARIANCE FOR HCO$_3$ (mM/L)

| | | |
|---|---|---|
| Total | 2189.69 | 149 |

DONOR SUM OF SQUARES = 2108.74
INTERACTION SS = DONOR SS − MECH SS − TIME SS
*DENOTES SIGNIFICANCE

STATISTICS TABLE 6
TWO WAY ANALYSIS OF VARIANCE FOR TCO$_2$ (mM/L)

DONOR SUMS

| MECH | \multicolumn{5}{c}{DAYS OF STORAGE} | MECH Σ | MECH X̄ | Dunnett's Test t-Value |
|---|---|---|---|---|---|---|---|---|
| | 1 | 7 | 14 | 21 | 28 | | | |
| 1 | 87.90 | 76.60 | 68.30 | 61.40 | 45.80 | 340.00 | 13.60 | −9.45 |
| 2 | 84.70 | 63.60 | 50.90 | 40.60 | 32.80 | 272.60 | 10.90 | |
| 3 | 79.70 | 64.00 | 48.70 | 40.70 | 30.60 | 263.70 | 10.55 | −10.68 |
| 4 | 87.70 | 58.20 | 46.50 | 38.90 | 31.10 | 262.40 | 10.50 | −10.85 |
| 5 | 83.70 | 54.60 | 39.20 | 31.30 | 22.20 | 231.00 | 9.124 | −15.26 |
| 6 | 69.80 | 47.70 | 36.60 | 29.00 | 22.00 | 205.10 | 8.20 | −18.90 |
| TIME Σ | 493.50 | 364.70 | 290.20 | 241.90 | 184.50 | | | |

ANOVA TABLE 6

| Source | Sum of Square | Degrees of Freedom | Mean Square | F Value |
|---|---|---|---|---|
| Mech | 415.87 | 5 | 83.17 | 81.54* |
| Time | 1910.71 | 4 | 477.68 | 468.31* |
| Interaction | 60.57 | 20 | 3.03 | 2.97* |
| Error | 121.81 | 120 | 1.02 | |
| Total | 2508.96 | 149 | | |

DONOR SUM OF SQUARES = 2387.15
INTERACTION SS = DONOR SS − MECH SS − TIME SS
*DENOTES SIGNIFICANCE

STATISTICS TABLE
TWO WAY ANALYSIS OF VARIANCE FOR Na$^{30}$ (mEq/L)

DONOR SUMS

| MECH | \multicolumn{5}{c}{DAYS OF STORAGE} | MECH Σ | MECH X̄ | Dunnett's Test t-Value |
|---|---|---|---|---|---|---|---|---|
| | 1 | 7 | 14 | 21 | 28 | | | |
| 1 | 921.00 | 893.00 | 860.00 | 868.00 | 846.00 | 4388.00 | 175.52 | |
| 2 | 918.00 | 823.00 | 776.00 | 768.00 | 728.00 | 4013.00 | 160.52 | −9.17 |
| 3 | 919.00 | 817.00 | 775.00 | 718.00 | 713.00 | 3942.00 | 157.68 | −10.91 |
| 4 | 916.00 | 810.00 | 745.00 | 713.00 | 685.00 | 3869.00 | 154.76 | −12.69 |
| 5 | 929.00 | 852.00 | 842.00 | 819.00 | 805.00 | 4247.00 | 169.88 | −3.45 |
| 6 | 853.00 | 807.00 | 758.00 | 697.00 | 649.00 | 3764.00 | 150.56 | −15.26 |
| TIME Σ | 5456.00 | 5002.00 | 4756.00 | 4583.00 | 4426.00 | | | |

ANOVA TABLE 7

| SOURCE | SUM OF SQUARES | DEGREES OF FREEDOM | MEAN SQUARE | F VALUE |
|---|---|---|---|---|
| Mech | 11,186.19 | 5 | 2237.24 | 66.88* |
| Time | 21,669.84 | 4 | 5417.46 | 161.96* |
| Interaction | 3,039.84 | 20 | 151.99 | 4.54* |
| Error | 4,013.60 | 120 | 33.45 | |
| Total | 39,909.47 | 149 | | |

DONOR SUM OF SQUARES = 35,895.87
INTERACTION SS = DONOR SS − MECH SS − TIME SS
*DENOTES SIGNIFICANCE

STATISTICS TABLE 8
TWO WAY ANALYSIS OF VARIANCE FOR K$^{30}$ (mEq/L)

DONOR SUMS

| MECH | \multicolumn{5}{c}{DAYS OF STORAGE} | MECH | MECH X̄ | Dunnett's Test Value 4 |
|---|---|---|---|---|---|---|---|---|
| | 1 | 7 | 14 | 21 | 28 | | | |
| 1 | 28.60 | 69.80 | 83.40 | 61.50 | 68.70 | 312.00 | 12.48 | |
| 2 | 33.20 | 62.80 | 68.90 | 69.00 | 70.90 | 304.80 | 12.19 | −0.86 |
| 3 | 36.50 | 68.50 | 69.00 | 69.00 | 69.00 | 312.00 | 12.48 | 0.00 |
| 4 | 39.00 | 68.70 | 69.00 | 69.00 | 69.00 | 314.70 | 12.59 | 0.33 |
| 5 | 30.00 | 82.40 | 67.50 | 69.00 | 69.00 | 317.90 | 12.72 | 0.71 |
| 6 | 31.50 | 61.30 | 83.80 | 90.10 | 61.20 | 327.90 | 13.12 | 1.91 |
| TIME Σ | 198.80 | 413.50 | 441.60 | 427.60 | 407.80 | | | |

ANOVA TABLE 8

| SOURCE | SUM OF SQUARES | DEGREES OF FREEDOM | MEAN SQUARE | F VALUE |
|---|---|---|---|---|

STATISTICS TABLE 8-continued

| | TWO WAY ANALYSIS OF VARIANCE FOR $K^{30}$ (mEq/L) | | | |
|---|---|---|---|---|
| Mech | 11.87 | 5 | 2.37 | 1.68 |
| Time | 1358.87 | 4 | 239.72 | 240.94* |
| Interaction | 225.62 | 20 | 11.28 | 8.00* |
| Error | 169.66 | 120 | 1.41 | |
| Total | 1766.03 | 149 | | |

DONOR SUM OR SQUARES = 1596.36
INTERACTION SS = DONOR SS -MECH SS - TIME SS
*DENOTES SIGNIFICANCE

STATISTICS TABLE 9

TWO WAY ANALYSIS OF VARIANCE FOR $PCO_2$ (mmHg)
DONOR SUMS

| MECH | DAYS OF STORAGE | | | | | MECH Σ | MECH X̄ | Dunnett's Test t-Value |
|---|---|---|---|---|---|---|---|---|
| | 1 | 7 | 14 | 21 | 28 | | | |
| 1 | 278.50 | 292.80 | 324.00 | 312.30 | 274.80 | 1482.40 | 59.30 | |
| 2 | 221.10 | 195.80 | 156.80 | 142.20 | 117.70 | 833/.60 | 33.34 | −16.14 |
| 3 | 166.10 | 162.10 | 122.40 | 105.30 | 74.10 | 630.00 | 25.20 | −21.21 |
| 4 | 164.40 | 129.60 | 93.30 | 70.90 | 51.90 | 510.10 | 20.40 | −24.19 |
| 5 | 202.00 | 146.70 | 118.70 | 105.50 | 82.70 | 655.60 | 26.22 | −20.57 |
| 6 | 323.40 | 233.00 | 219.80 | 190.80 | 163.70 | 1130.70 | 45.23 | −8.75 |
| TIME 93 | 1355.50 | 1160.00 | 1035.00 | 927.00 | 764.90 | | | |

ANOVA TABLE 9

| SOURCE | SUM OF SQUARES | DEGREES OF FREEDOM | Mean square | F VALUE |
|---|---|---|---|---|
| Mech | 27,093.40 | 5 | 5,418.68 | 167.66* |
| Time | 6,735.16 | 4 | 1,683.79 | 52.10* |
| Interaction | 2,483.01 | 20 | 124.15 | 3.84* |
| Error | 3,878.92 | 120 | 32.32 | |
| Total | 40,190.49 | 149 | | |

DONOR SUM OF SQUARES = 36,311.57
INTERACTION SS = DONOR SS - MECH SS - TIME SS
*DENOTES SIGNIFICANCE

STATISTICS TABLE 10

TWO WAY ANALYSIS OF VARIANCE FOR $PO_2$ (mmHg)
DONOR SUMS

| MECH | DAYS OF STORAGE | | | | | MECH Σ | MECH X̄ | Dunnett's Test t-Value |
|---|---|---|---|---|---|---|---|---|
| | 1 | 7 | 14 | 21 | 28 | | | |
| 1 | 253.20 | 275.50 | 351.00 | 682.40 | 1000.20 | 2562.30 | 102.49 | |
| 2 | 205.40 | 274.30 | 550.00 | 682.50 | 862.10 | 2574.30 | 102.97 | 0.05 |
| 3 | 207.30 | 230.20 | 427.80 | 479.40 | 888.00 | 2232.70 | 89.31 | −1.34 |
| 4 | 220.70 | 233.60 | 297.70 | 367.10 | 804.70 | 1923.80 | 76.95 | −2.60 |
| 5 | 206.30 | 285.40 | 597.90 | 767.90 | 861.10 | 2718.60 | 108.74 | 0.64 |
| 6 | 273.20 | 30.30 | 786.60 | 653.90 | 877.50 | 2921.50 | 116.86 | 1.47 |
| TIME Σ | 1366.10 | 1629.30 | 3011.00 | 3633.20 | 5293.60 | | | |

ANOVA TABLE 10

| SOURCE | SUM OF SQUARES | DEGREES OF FREEDOM | MEAN SQUARE | F VALUE |
|---|---|---|---|---|
| Mech | 25,502.48 | 5 | 5100.50 | 4.24* |
| Time | 340,307.32 | 4 | 85076.83 | 70.76* |
| Interaction | 36,023.57 | 20 | 1801.18 | 1.50 |
| Error | 144,276.12 | 120 | 1202.30 | |
| Total | 546,109.49 | 149 | | |

DONOR SUM OF SQUARE = 401,833.37
INTERACTION SS = DONOR SS - MECH SS - TIME SS
*DENOTES SIGNIFICANCE

APPENDIX C

Statistical Procedures
Figure 1-0

Notation:
- c = number of times
- r = number of mechanisms
- n = number of subjects
- $X_{i..}$ = sum for the ith time
- $\bar{X}_{i..}$ = mean for the ith time = $\frac{X_{i..}}{rn}$
- $X_{.j.}$ = sum for the jth mechanism
- $\bar{X}_{.j.}$ = mean for the jth mechanism = $\frac{X_{.j.}}{cn}$
- $X_{...}$ = overall sum

APPENDIX C-continued $$\bar{X}... = \frac{X...}{crn}$$

TWO WAY ANALYSIS OF VARIANCE

| Source | Sum of Squares | Degrees of Freedom (df) | Mean Square | F-Value |
|---|---|---|---|---|
| Time | $rn\Sigma(\bar{X}_{i..} - \bar{X}...)^2 = S_c$ | $c - 1$ | $\frac{S_c}{(c-1)} = M_c$ | $\frac{M_c}{M_E}$ |
| Mechanism | $cn\Sigma(\bar{X}.j.  - \bar{X}...)^2 = S_r$ | $r - 1$ | $\frac{S_r}{r-1} = M_c$ | $\frac{M_r}{M_E}$ |
| Interaction | $S_s - S_c - S_r = S_1$ | $(c-1)(r-1)$ | $\frac{S_1}{(c-1)(r-1)} = M_I$ | $\frac{M_I}{M_E}$ |
| Subtotal | $n\Sigma\Sigma(\bar{X}_{ij.} - \bar{X}...)^2 = S_S$ | $rc(n-1)$ | | |
| Error | $S_T - S_S = S_E$ | $rc(n-1)$ | $\frac{S_E}{rc(n-1)} = M_E$ | |
| Total | $\Sigma\Sigma\Sigma(X_{ije} - \bar{X}...)^2 = S_T$ | $rcn - 1$ | | |

Pertinent F Values derived from F Table $\frac{n=5}{n>120} = 2.29 \quad \frac{n=4}{n=120} = 2.45 \quad \frac{n=20}{n=120} = 1.66$ Ref. Dixon, Wilfred. Massey, Frank. Introduction to
Statistical Analysis. McGraw-Hill Book Co., Inc.,
1957.

Prodecure 1-1 Dunnett's Test $$t = \frac{\Delta}{SE_\Delta}$$

$$SE_\Delta = \sqrt{\frac{2 \text{ Error Mean Square}}{25}}$$

$\Delta$ = Mech mean − Control mean
$t > 2.89$ ($p < .01$), 99% confidence level
$t > 2.26$ ($p < .05$), 95% confidence level
All statistical calculations were performed on
the Hewlett Packard JP 65 Calculator
Dunnett's test should be used when the research involves
multiple comparison of several treatments or systems with
the same control (25).

NOTE: 25 = Number of observatins per mechanism calculated by multiplying the number of donors times the number of days the specimens were aliquoted off.

---

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a composition of matter comprising metabolizing erythrocytes in an in vitro environment capable of supporting erythrocyte metabolism, the improvement which comprises a water-insoluble polymer containing releaseable phosphate ions for supplying a physiologically acceptable, continuous, sustained release source of metabolizable phosphate to said erythrocytes in an amount sufficient to maintain both 2,3DPG and ATP levels at least equal to those of freshly drawn blood for a storage period equivalent to 28 days of storage at 4° C.

2. A composition according to claim 1, wherein said environment includes a safe and effective amount of an anticoagulant.

3. A composition according to claim 2, wherein said environment includes packed blood cells substantially free of plasma.

4. A composition according to claim 2, wherein said environment includes whole blood.

5. A composition according to claim 2, wherein said anticoagulant is citrate-phosphate-dextrose.

6. A composition according to claim 1, wherein said water-insoluble polymer is particulate.

7. A composition according to claim 6, wherein said polymer is an ion exchange resin.

8. A composition according to claim 7, wherein said polymer is a weakly basic anion exchange resin.

9. A composition according to claim 8, wherein said metabolizable phosphate is inorganic dibasic phosphate $HPO_4^{--}$.

10. A composition according to claim 8, wherein said environment includes a safe and effective amount of anticoagulant.

11. A composition according to claim 10, wherein said erythrocytes are human erythrocytes.

12. A composition according to claim 11, wherein said anticoagulant is citrate-phosphate-dextrose.

13. A composition according to claim 10, wherein said in vitro environment is within a sterile blood collection container.

14. In an article of manufacture comprising a sterile blood collection and storage container having a safe and effective amount of anticoagulant therein, the improvement which comprises a water-insoluble polymer containing releasable phosphate ions for supplying a continuous, sustained release source of metabolizable phosphate to metabolizing erythrocytes in an amount sufficient to maintain both 2,3DPG and ATP levels of collected blood at least equal to those of freshly drawn blood for a storage period equivalent to 28 days of storage at 4° C.

15. An article according to claim 14, wherein said water-insoluble polymer is particulate.

16. An article according to claim 15, wherein said polymer is an ion exchange resin.

17. An article according to claim 16, wherein said polymer is a weakly basic anion exchange resin.

18. In a method for maintaining metabolizing erythrocytes suitable for transfusion in a sterile container, the improvement which comprises adding to said container a water-insoluble polymer containing releasable phosphate ions for supplying a continuous source of metabolizable phosphate to said metabolizing erythrocytes in an amount sufficient to maintain both 2,3DPG and ATP levels at least equal to those of freshly drawn blood for a storage period equivalent to 28 days of storage at 4° C.

19. A method according to claim 18, wherein said water-insoluble polymer is particulate.

20. A method according to claim 19, wherein said polymer is an ion exchange resin.

21. A method according to claim 20, wherein said polymer is a weakly basic anion exchange resin.

22. A storable, transfusable composition of matter comprising metabolizing erythrocytes in an in vitro environment capable of supporting erythrocyte metabolism having incorporated therein a water-insoluble polymer containing releaseable phosphate ions capable of continuously supplying metabolizable phosphate to said erythrocytes.

23. A composition according to claim 22, wherein said water-insoluble polymer is particulate.

24. A composition according to claim 23, wherein said polymer is an ion exchange resin.

* * * * *